(12) United States Patent
Nicolas-Morgantini et al.

(10) Patent No.: US 7,695,526 B2
(45) Date of Patent: Apr. 13, 2010

(54) COMPOSITION FOR THE OXIDATION DYEING OF KERATIN FIBERS, COMPRISING, AT LEAST ONE OXIDATION DYE, AT LEAST ONE FATTY ALCOHOL, AT LEAST ONE ASSOCIATIVE POLYMER, AND AT LEAST ONE C14-C30 ALKYL SULPHATE

(75) Inventors: Luc Nicolas-Morgantini, Rully (FR); Frédéric Simonet, Touqin (FR); Christine Rondeau, Sartrouville (FR); François Cottard, Courbevoie (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 11/907,406

(22) Filed: Oct. 11, 2007

(65) Prior Publication Data

US 2008/0168609 A1    Jul. 17, 2008

Related U.S. Application Data

(63) Continuation of application No. 10/729,014, filed on Dec. 8, 2003, now abandoned.

(60) Provisional application No. 60/502,218, filed on Sep. 12, 2003.

(30) Foreign Application Priority Data

Dec. 6, 2002    (FR)    ................................ 02 15474

(51) Int. Cl.
    *A61Q 5/10*    (2006.01)
(52) U.S. Cl. ................... 8/405; 8/406; 8/408; 8/409; 8/410; 8/411; 8/412; 8/552; 8/554; 8/555; 8/558
(58) Field of Classification Search ............ 8/405, 8/406, 408, 409, 410, 411, 412, 552, 554, 8/555, 558
    See application file for complete search history.

(56) References Cited

U.S. PATENT DOCUMENTS

| | | | |
|---|---|---|---|
| 3,836,326 A * | 9/1974 | Sokol et al. ................... | 8/415 |
| 4,201,766 A | 5/1980 | Grollier et al. | |
| 6,056,947 A | 5/2000 | Kahre et al. | |
| 6,555,101 B1 | 4/2003 | Kahre et al. | |
| 7,101,405 B2 | 9/2006 | Cottard et al. | |
| 7,364,594 B2 | 4/2008 | Cottard et al. | |
| 2001/0023514 A1 * | 9/2001 | Cottard et al. ................ | 8/406 |
| 2002/0046431 A1 * | 4/2002 | Laurent et al. ................ | 8/405 |

FOREIGN PATENT DOCUMENTS

| | | |
|---|---|---|
| DE | 200 18 140 | 3/2001 |
| EP | 0 943 317 A2 | 9/1999 |
| GB | 2024873 | 1/1980 |
| WO | WO 94/01076 A1 | 1/1994 |
| WO | WO 00/69400 | 12/2000 |
| WO | WO 02/38115 | 5/2002 |
| WO | WO 02/38116 A1 | 5/2002 |
| WO | WO 02/45674 A1 | 6/2002 |
| WO | WO 02/092035 A1 | 11/2002 |

OTHER PUBLICATIONS

English language Derwent Abstract of DE 200 18 140, (2001).
English language Derwent Abstract of EP 0 943 317 A2, (1999).

* cited by examiner

*Primary Examiner*—Eisa B Elhilo
(74) *Attorney, Agent, or Firm*—Finnegan Henderson Farabow Garrett & Dunner LLP

(57) ABSTRACT

A composition for the oxidation dyeing of keratin fibers, for example, human keratin fibers, such as hair, comprising, in a medium suitable for dyeing,
    a) at least one oxidation dye,
    b) at least one fatty alcohol,
    c) at least one associative polymer, and
    d) at least one $C_{14}$-$C_{30}$ alkyl sulphate; as well as the process for using this composition and multicompartment kits comprising the composition.

89 Claims, No Drawings

1

COMPOSITION FOR THE OXIDATION DYEING OF KERATIN FIBERS, COMPRISING, AT LEAST ONE OXIDATION DYE, AT LEAST ONE FATTY ALCOHOL, AT LEAST ONE ASSOCIATIVE POLYMER, AND AT LEAST ONE C14-C30 ALKYL SULPHATE

This application is a continuation of a U.S. application Ser. No. 10/729,014, filed Dec. 8,2003, now abandoned, and claims the benefit of U.S. provisional application No. 60/502, 218, filed Sep. 12, 2003, which is incorporated herein by reference.

Disclosed herein is a composition for the oxidation dyeing of keratin fibers, for example, human keratin fibers. such as hair, comprising at least one oxidation dye, at least one fatty alcohol, at least one associative polymer and at least one $C_{14}$-$C_{30}$ alkyl sulphate.

It is known practice to dye keratin fibers, such as human hair, with dye compositions comprising oxidation dye precursors, generally known as "oxidation bases", such as, ortho- or para-phenylenediamines, ortho- or para-aminophenols, and heterocyclic bases.

Oxidation dye precursors are compounds which are initially uncolored or only weakly colored and which develop their dyeing power on the hair in the presence of oxidizing agents, leading to the formation of colored compounds. The formation of these colored compounds may result either from an oxidative condensation of the "oxidation bases" with themselves or from an oxidative condensation of the "oxidation bases" with coloration modifiers, or "couplers", which may be present in the dye compositions used in oxidation dyeing and are represented, for example, by meta-phenylenediamines, meta-aminophenols and meta-diphenols, and certain heterocyclic compounds.

The variety of molecules used, which include on the one hand the "oxidation bases" and on the other hand the "couplers," can allow a very wide range of colors to be obtained.

Compositions which comprise oxidation dyes and that are mixed before use with an oxidizing agent can often be provided in the form of water-based creams conventionally comprising fatty alcohols and occasionally soaps. These creams may have a high fatty alcohol and crosslinked polyacrylic acid content in order to ensure the consistency and stability of the medium.

The present inventors, however, have noted that this high fatty alcohol content can lead to a change in viscosity of the tinctorial composition over time, which can be manifested in a reduction in the ease of mixing with the oxidizing agent and in an impairment of the usage qualities such as elimination on rinsing.

However, following substantial research, the present inventors have now found that oxidation dye compositions comprising at least one oxidation dye, at least one fatty alcohol, at least one associative polymer and at least one $C_{14}$-$C_{30}$ alkyl sulphate can have a satisfactory consistency and a viscosity which may be stable over time without the need to raise the concentration of fatty alcohols or to use other thickening agents of the crosslinked polyacrylic acid type.

This discovery forms the basis of the various embodiments disclosed herein.

Disclosed herein is thus a composition for the oxidation dyeing of keratin fibers, for example, human keratin fibers, such as hair, comprising, in a medium suitable for dyeing,
a) at least one oxidation dye,
b) at least one fatty alcohol,
c) at least one associative polymer, and
d) at least one $C_{14}$-$C_{30}$ alkyl sulphate.

2

Further disclosed herein is a ready-to-use composition for the dyeing of keratin fibers comprising at least one oxidation dye, at least one fatty alcohol, at least one associative polymer, at least one $C_{14}$-$C_{30}$ alkyl sulphate and at least one oxidizing agent.

As used herein, the expression "ready-to-use composition" means the composition is intended for application as is to the keratin fibers; that is to say, it may be stored as is before use or may result from the extemporaneous mixing of two or more compositions.

Further disclosed herein is a process for the oxidation dyeing of keratin fibers, for example, human keratin fibers such as hair, comprising applying to the fibers at least one composition (A) comprising, in a medium that is suitable for dyeing, at least one oxidation dye, at least one fatty alcohol, at least one associative polymer, and at least one $C_{14}$-$C_{30}$ alkyl sulphate, the color being developed at alkaline, neutral or acidic pH, by means of at least one composition (B) comprising at least one oxidizing agent, which is mixed with the composition (A) at the time of use or which is applied to the fibers sequentially before or after composition (A), with or without intermediate rinsing.

Further disclosed herein are multi-compartment dyeing devices or multi-compartment kits for the oxidation dyeing of keratin fibers, for example, human keratin fibers such as hair. This device may comprise a first compartment comprising at least one oxidation dye, at least one fatty alcohol chosen from possibly oxyalkylenated and glycerolated fatty alcohols, at least one associative polymer, and at least one $C_{14}$-$C_{30}$ alkyl sulphate, and a second compartment comprising at least one oxidizing agent.

Other features, aspects, subjects and advantages of the embodiments disclosed herein will emerge even more clearly on reading the description and the examples that follow, without, however, being limiting in nature.

$C_{14}$-$C_{30}$ Alkyl Sulphates

The at least one $C_{14}$-$C_{30}$ alkyl sulphate may, for example, be chosen from:
  sodium cetostearyl sulphate, such as the product sold under the commercial name LANETTE E by the company Cognis and
  sodium myristyl sulphate, such as the product sold under the commercial name NIKKOL SMS-F by the company Nikko.

The at least one $C_{14}$-$C_{30}$ alkyl sulphate may, for example, be present in the composition disclosed herein in an amount ranging from 0.1% to 10% by weight, relative to the total weight of the composition, and further, for example, from 0.5% to 5% by weight, relative to the total weight of the composition.

Associative Polymers

The at least one associative polymer is a polymer whose molecules are capable, in the formulation medium, of undergoing association with one another or with molecules of other compounds.

For example, one type of associative polymers that can be used in the composition disclosed herein are amphiphilic polymers, i.e. polymers comprising at least one hydrophilic moiety which render them soluble in water and at least one hydrophobic region, comprising at least one fatty chain, by means of which the polymers interact and undergo assembly with one another or with other molecules.

The at least one associative polymer disclosed herein may, for example, be chosen from non-ionic, anionic, cationic and amphoteric associative polymers.

The at least one associative polymer disclosed herein may, for example, be chosen from associative polymers comprising at least one fatty chain. The at least one fatty chain may comprise, for example, from 8 to 30 carbon atoms and, further, for example, from 10 to 30 carbon atoms.

Anionic Polymers

For example, the anionic polymers comprising at least one fatty chain may be chosen from:

(I) polymers comprising at least one hydrophilic unit and at least one fatty-chain allyl ether unit, for example, those polymers whose at least one hydrophilic unit comprises at least one ethylenic unsaturated anionic monomer, such as a vinylcarboxylic acid and further, such as, an acrylic acid or a methacrylic acid, and wherein the at least one fatty-chain allyl ether unit may, for example, be chosen from monomers of formula (I) below:

$$CH_2=CR'CH_2OB_nR \qquad (I)$$

wherein:
R' is chosen from H and $CH_3$;
B is an ethyleneoxy radical;
n is equal to zero or is an integer ranging from 1 to 100; and
R is a hydrocarbon-based radical chosen from alkyl, arylalkyl, aryl, alkylaryl and cycloalkyl radicals, comprising from 8 to 30 carbon atoms, for example, 10 to 24 carbon atoms and even further, for example, from 12 to 18 carbon atoms. A unit of formula (I) that can, for example, be used is a unit wherein R' is H, n is equal to 10 and R is a stearyl ($C_{18}$) radical.

Anionic amphiphilic polymers of this type are described and prepared, according to an emulsion polymerization process, in Patent No. EP-0 216 479.

For example, the anionic associative polymers comprising at least one fatty chain that can be used in the composition disclosed herein may be chosen from polymers formed from 20% to 60% by weight of acrylic acid and/or of methacrylic acid, from 5% to 60% by weight of lower alkyl(meth)acrylates, from 2% to 50% by weight of at least one fatty-chain allyl ether of formula (I), and from 0% to 1% by weight of a crosslinking agent which is a well-known copolymerizable unsaturated polyethylenic monomer, such as diallyl phthalate, allyl(meth)acrylate, divinylbenzene, (poly)ethylene glycol dimethacrylate or methylenebisacrylamide.

Among the latter polymers, those that can, for example, be used in the composition disclosed herein may be chosen from crosslinked terpolymers of methacrylic-acid, of ethyl acrylate and of polyethylene glycol (10 EO) stearyl ether alcohol (Steareth-10), such as those sold by the company Allied Colloids under the names Salcare SC 80® and Salcare SC 90®, which are aqueous 30% emulsions of a crosslinked terpolymer of methacrylic acid, of ethyl acrylate and of steareth-10 alkyl ether (40/50/10).

(II) polymers comprising at least one hydrophilic unit of unsaturated olefinic carboxylic acid and at least one hydrophobic unit of unsaturated carboxylic acid ($C_{10}$-$C_{30}$)alkyl ester. For example, these polymers are chosen from those in which the hydrophilic unit of unsaturated olefinic carboxylic acid corresponds to the monomer of formula (II) below:

wherein $R_1$ is chosen from H, $CH_3$, and $C_2H_5$, for example, acrylic acid, methacrylic acid and ethacrylic acid units, and wherein the at least one hydrophobic unit of unsaturated carboxylic acid ($C_{10}$-$C_{30}$)alkyl ester is chosen from monomers of formula (III) below:

wherein:
$R_2$ is chosen from H, $CH_3$, and $C_2H_5$, for example, acrylate, methacrylate and ethacrylate units and, further, for example, H (acrylate units) and $CH_3$ (methacrylate units) and
$R_3$ is chosen from $C_{10}$-$C_{30}$ alkyl radicals, for example, $C_{12}$-$C_{22}$ alkyl radicals.

The ($C_{10}$-$C_{30}$) alkyl esters of unsaturated carboxylic acids disclosed herein may, for example, be chosen from lauryl acrylate, stearyl acrylate, decyl acrylate, isodecyl acrylate and dodecyl acrylate, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

The anionic polymers of this type may, for example, be chosen from polymers formed from a monomer mixture comprising:
(i) essentially acrylic acid,
(ii) at least one ester of formula (III) described above wherein $R_2$ is chosen from H and $CH_3$, $R_3$ is chosen from alkyl radicals comprising from 12 to 22 carbon atoms, and
(iii) at least one crosslinking agent, which is a well-known copolymerizable polyethylenic unsaturated monomer, such as diallyl phthalate, allyl(meth)acrylate, divinylbenzene, (poly)ethylene glycol dimethacrylate and methylenebisacrylamide.

The anionic polymers comprising at least one fatty chain of this type may, for example, be chosen from polymers comprising from 60% to 95% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those monomers comprising from 96% to 98% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

These polymers may, for example, be chosen from products sold by the company Goodrich under the trade names PEMULEN TR1, PEMULEN TR2 and CARBOPOL 1382, and further, for example, PEMULEN TR1, and the product sold by the company SEPPIC under the name COATEX SX.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name PERFORMA V 1608 by the company Newphase Technologies.

(IV) acrylic terpolymers comprising:
(a) from 20% to 70% by weight of a carboxylic acid containing α,β-monoethylenic unsaturation,
(b) from 20% to 80% by weight of a non-surfactant monomer containing α,β-monoethylenic unsaturation and being other than (a), (c) from 0.5% to 60% by weight of a non-ionic monourethane which is the product of reaction of a monohydric surfactant with a monoisocyanate containing monoethylenic unsaturation, such as those described in Patent Application No. EP-A-0 173 109 and further, for example, the terpolymer described in Example 3, namely a methacrylic acid/methyl acrylate/ethoxylated (40 EO) behenyl dimethyl-meta-isopropenyl-benzylisocyanate terpolymer, as an aqueous 25% dispersion.

(V) copolymers comprising among their monomers at least one carboxylic acid containing α,β-monoethylenic unsaturation and at least one ester of a carboxylic acid containing α,β-monoethylenic unsaturation and of an oxyalkylenated fatty alcohol.

For example, these compounds can also comprise as a monomer an ester of a carboxylic acid containing α,β-monoethylenic unsaturation and of a $C_1$-$C_4$ alcohol.

ACULYN 22 sold by the company Rohm & Haas, a methacrylic acid/ethyl acrylate/stearyl methacrylate oxyalkylenated terpolymer, is an example of a compound of this type.

Non-Ionic Polymers

The non-ionic amphiphilic polymers comprising at least one fatty chain that can used in the composition disclosed herein may, for example, be chosen from:

(1) celluloses modified with groups comprising at least one fatty chain; for example:

hydroxyethylcelluloses modified with at least one group comprising at least one fatty chain, for example, the at least one group may be chosen from alkyl, arylalkyl and alkylaryl groups, wherein the alkyl groups may, for example, be chosen from $C_8$-$C_{22}$ groups, such as the product NATROSOL PLUS GRADE 330 CS($C_{16}$ alkyls) sold by the company Aqualon, and the product BERMOCOLL EHM 100 sold by the company Berol Nobel, and celluloses modified with alkylphenyl polyalkylene glycol ether groups, such as the product AMERCELL POLYMER HM-1500 (nonylphenyl polyethylene glycol (15) ether) sold by the company Amerchol.

(2) hydroxypropylguars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia.

(3) copolymers of vinylpyrrolidone and of fatty-chain hydrophobic monomers, for example:

the products ANTARON V216 or GANEX V216 (vinylpyrrolidone/hexadecene copolymer) sold by the company I.S.P.

the products ANTARON V220 or GANEX V220 (vinylpyrrolidone/eicosene copolymer) sold by the company ISP.

(4) copolymers of $C_1$-$C_6$ alkyl methacrylates or acrylates and of amphiphilic monomers comprising at least one fatty chain, such as, the oxyethylenated methyl acrylate/stearyl acrylate copolymer sold by the company Goldschmidt under the name ANTIL 208.

(5) copolymers of hydrophilic methacrylates or acrylates and of hydrophobic monomers comprising at least one fatty chain, such as, a polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton comprising at least one fatty chain, such as the PURE THIX compounds sold by the company Sud-Chemie.

For example, the polyurethane polyethers can comprise at least two hydrocarbon-based lipophilic chains comprising from 8 to 30 carbon atoms, separated by a hydrophilic block, the hydrocarbon-based chains possibly being pendent chains or chains at the end of the hydrophilic block. For example, it is possible for at least one pendent chain to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The polyurethane polyethers may be triblock copolymers in which the hydrophilic block is a polyoxyethylenated chain comprising from 50 to 1 000 oxyethylene groups. The polyurethane polyethers may comprise a urethane linkage between the hydrophilic blocks, whence arises the name.

By extension, also included among the polyurethane polyethers are those polymers in which the hydrophilic blocks are linked to the lipophilic blocks via other chemical bonds.

For example, the polyurethane polyethers that may be used in the composition disclosed herein, may be chosen from RHEOLATE 205 comprising at least one urea functional group, sold by the company Rheox, and the RHEOLATES 208, 204 and 212, and also ACRYSOL RM 184, ACULYN 46 and ACULYN 44 from the company Rohm & Haas [ACULYN 46 is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and water (81%); ACULYN 44 is a polycondensate of polyethylene glycol comprising 150 or 180 mol of ethylene oxide, of decyl alcohol and of methylenebis(4-cyclohexylisocyanate) (SMDI), at 35% by weight in a mixture of propylene glycol (39%) and water (26%)].

The product ELFACOS T210 comprising at least one $C_{12\text{-}14}$ alkyl chain, and the product ELFACOS T212 comprising at least one $C_{18}$ alkyl chain, from Akzo may also be used in the composition disclosed herein.

Further, the product DW 1206B from Rohm & Haas comprising at least one $C_{20}$ alkyl chain and a urethane linkage, sold at a solids content of 20% in water, may also be used.

It is also possible to use solutions or dispersions of these polymers, for example, in water or in aqueous alcoholic medium. Examples of such polymers that may be mentioned are RHEOLATE 255, RHEOLATE 278 and RHEOLATE 244 sold by the company Rheox. The products DW 1206F and DW 1206J sold by the company Rohm & Haas may also be used. The polyurethane polyethers that may be used in the composition disclosed herein are those described in the article by G. Formum, J. Bakke and Fk. Hansen, Colloid Polym. Sci 271, 380.389 (1993).

Cationic Polymers

The cationic polymers comprising at least one fatty chain that can be used in the composition disclosed herein may, for example, be chosen from quaternized cellulose derivatives, polyacrylates comprising non-cyclic amine side groups, cationic polyurethanes, cationic polyvinyllactams and the acrylic terpolymer whose constitution is given below.

The quaternized cellulose derivatives may, for example, be chosen from:

quaternized celluloses modified with at least one group comprising at least one fatty chain, for example, the at least one group may be chosen from alkyl, arylalkyl and alkylaryl groups comprising at least 8 carbon atoms, quaternized hydroxyethylcelluloses modified with at least one group comprising at least one fatty chain, for example, the at least one group may be chosen from alkyl, arylalkyl and alkylaryl groups comprising at least 8 carbon atoms.

The alkyl groups borne by the above quaternized celluloses or hydroxyethylcelluloses may, for example, comprise from 8 to 30 carbon atoms. The aryl groups may, for example, be chosen from phenyl, benzyl, naphthyl and anthryl groups.

Examples of alkylhydroxyethylcelluloses quaternized with $C_8$-$C_{30}$ fatty chains include quaternized hydroxyethylcelluloses modified with at least one group chosen from $C_{12}$ and $C_{18}$ alkyl groups, such as the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) which is sold by the company Amerchol and the products CRODACEL QM, CRODACEL QL ($C_{12}$ alkyl) and CRODACEL QS ($C_{18}$ alkyl) which is sold by the company Croda.

The polyacrylates comprising non-cyclic amine side groups, quaternized or non-quaternized, comprise, for example, hydrophobic groups of the steareth 20 type (polyoxyethylenated (20) stearyl alcohol).

Examples of polyacrylates comprising amine side chains include the polymers 8781-121B or 9492-103 provided by the company National Starch.

The cationic associative polyurethanes that can be used in the composition disclosed herein may, for example, be chosen from cationic associative amphiphilic polyurethanes, which are water-soluble or water-dispersible.

The term "water-soluble" or "soluble in water" in relation to the cationic associative amphiphilic polyurethanes disclosed herein means that these polymers have a solubility in water at ambient temperature of at least 1% by weight; that is to say that, up to this concentration, no precipitate can be detected by the naked eye and the solution is perfectly clear and homogeneous.

Polyurethanes which are "water-dispersible" or "dispersible in water" are polymers which, when suspended in water, spontaneously form droplets having an average size, as measured by light scattering on a Coulter-type apparatus, ranging, for example, from 5 nm to 600 nm, and further, for example, ranging from 5 nm to 500 nm.

The family of cationic amphiphilic polyurethanes disclosed herein have been described in French Patent Application No. 0 009 609; this family may be represented by the general formula (IV) below:

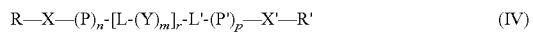

R—X—(P)$_n$-[L-(Y)$_m$]$_r$-L'-(P')$_p$—X'—R'    (IV)

wherein:

R and R', which may be identical or different, are each chosen from hydrophobic groups and a hydrogen atom;

X and X', which may be identical or different, are each chosen from groups comprising at least one amine functional group optionally bearing at least one hydrophobic group, or alternatively groups L";

L, L' and L", which may be identical or different, are each chosen from groups derived from a diisocyanate;

P and P', which may be identical or different, are each chosen from groups comprising at least one amine functional group optionally bearing at least one hydrophobic group;

Y is chosen from hydrophilic groups;

r is an integer ranging from 1 to 100, for example, from 1 to 50 and further, for example, from 1 to 25, n, m and p, which may be identical or different, are each integers ranging from 0 to 1000; and wherein the molecule comprises at least one functional group chosen from protonated and quaternized amine functional groups and hydrophobic groups.

In one embodiment of the polyurethanes disclosed herein, the only hydro-phobic groups are the groups R and R' at the chain ends.

For example, one family of cationic amphiphilic polyurethanes that can be used in the composition disclosed herein, for example, is the one corresponding to formula (IV) described above wherein:

R and R', which may be identical or different, are each chosen from hydro-phobic groups, X and X', which may be identical or different, are each chosen from groups L", n and p, which may be identical or different, are each integers ranging from 1 to 1000, and L, L', L", P, P', Y and m have the meaning given above.

Another family of cationic amphiphilic polyurethanes which can be used in the composition disclosed herein, for example, is the one corresponding to formula (IV) above wherein:

R and R', which may be identical or different, are each chosen from hydrophobic groups, X and X', which may be identical or different, are each chosen from groups L", n and p are equal to 0, and L, L', L", Y and m have the meaning given above.

The fact that n and p are 0 means that these polymers do not comprise units derived from a monomer comprising at least one amine functional group incorporated into the polymer during the polycondensation. The protonated amine functional groups of these polyurethanes result from the hydrolysis of excess isocyanate functional groups, at the chain end, followed by alkylation of the primary amine functional groups formed with alkylating agents comprising at least one hydrophobic group, i.e. compounds of the type RQ or R'Q, wherein R and R' are as defined above and Q is chosen from leaving groups such as a halide, a sulphate, etc.

Yet another family of cationic amphiphilic polyurethanes that can be used in the composition disclosed herein, for example, is the one corresponding to formula (IV) above wherein:

R and R', which may be identical or different, are each chosen from hydro-phobic groups, X and X', which may be identical or different, are each chosen from groups comprising at least one quaternary amine group, n and p are equal to 0, and L, L', Y and m have the meaning given above.

The number-average molecular mass of the cationic associative polyurethanes may, for example, range from 400 to 500 000, further, for example, from 1000 to 400 000 and even further, for example, from 1000 to 300 000.

As used herein, the expression "hydrophobic group" means a radical or polymer comprising at least one chain chosen from saturated and unsaturated, linear and branched hydrocarbon-based chains, which may comprise at least one entity chosen from heteroatoms such as P, O, N or S and radicals comprising at least one chain chosen from perfluoro and silicone chains. When the hydrophobic group is chosen from hydrocarbon-based radicals, it may comprise at least 10 carbon atoms, for example, from 10 to 30 carbon atoms, further, for example, from 12 to 30 carbon atoms and even further, for example, from 18 to 30 carbon atoms.

In one embodiment, the hydrocarbon-based radicals can be derived from a monofunctional compound.

For example, the hydrophobic group may be derived from a fatty alcohol such as stearyl alcohol, dodecyl alcohol or decyl alcohol. It may also be a hydrocarbon-based polymer such as, polybutadiene.

When X and/or X' are chosen from groups comprising at least one group chosen from tertiary and quaternary amine groups, X and/or X' may represent one of the following formulae:

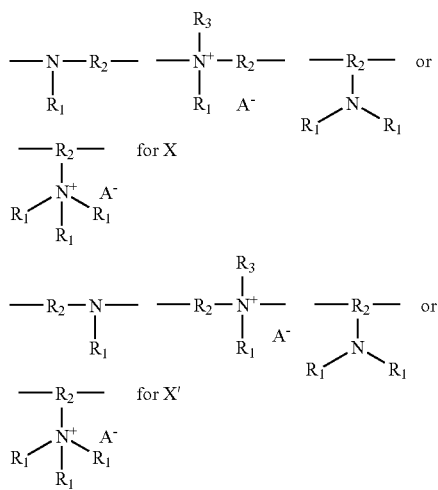

wherein:

$R_2$ is chosen from linear and branched alkylene radical comprising from 1 to 20 carbon atoms, optionally comprising at least one entity chosen from saturated and unsaturated rings and an arylene radical, at least one of the carbon atoms possibly being replaced with a heteroatom chosen from N, S, O and P;

$R_1$ and $R_3$, which may be identical or different, are each chosen from linear and branched $C_1$-$C_{30}$ alkyl and alkenyl radicals and aryl radicals, at least one of the carbon atoms in said radicals possibly being replaced with a heteroatom chosen from N, S, O and P; and $A^-$ is a physiologically acceptable counter-ion.

The groups L, L' and L", which may be identical or different, each represent a group of formula:

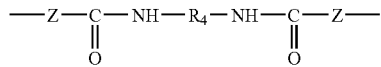

wherein:

Z is chosen from —O—, —S— and —NH—; and $R_4$ is chosen from linear and branched alkylene radicals comprising from 1 to 20 carbon atoms, optionally comprising at least one entity chosen from saturated and unsaturated rings and an arylene radical, at least one of the carbon atoms possibly being replaced with at least one heteroatom chosen from N, S, O and P.

In formula (IV), the groups P and P', which may be identical or different, comprising at least one amine functional group, may represent at least one of the following formulae:

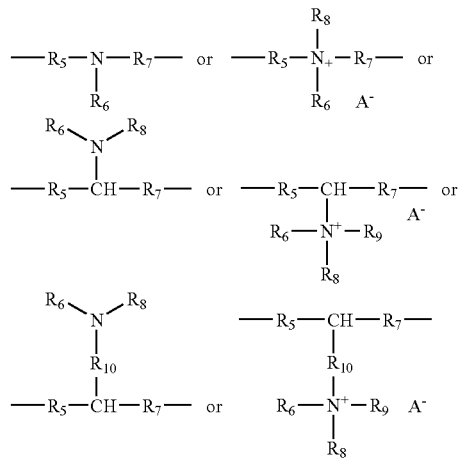

wherein:

$R_5$ and $R_7$, which may be identical or different, have the same meanings as $R_2$ defined above;

$R_6$, $R_8$ and $R_9$, which may be identical or different, have the same meanings as $R_1$ and $R_3$ defined above;

$R_{10}$ is chosen from linear and branched, optionally unsaturated alkylene groups which may comprise at least one heteroatom chosen from N, O, S and P, and $A^-$ is a physiologically acceptable counter-ion.

With regard to the meaning of Y, as used herein, the term "hydrophilic group" means a polymeric or non-polymeric water-soluble group.

For example, when the hydrophilic group is not a polymer, it may be chosen from ethylene glycol, diethylene glycol and propylene glycol.

When the hydrophilic group is a hydrophilic polymer, in accordance with one embodiment disclosed herein, it may, for example, be chosen from at least one of polyethers, sulphonated polyesters, and sulphonated polyamides. The hydrophilic polymer may, for example, be a polyether and further, for example, a poly(ethylene oxide) or a poly(propylene oxide).

The cationic associative polyurethanes of formula (IV) disclosed herein may be formed from diisocyanates and from various compounds with at least one functional group comprising labile hydrogen. The at least one functional groups comprising labile hydrogen may, for example, be chosen from alcohol, primary and secondary amine and thiol functional groups giving, after reaction with the diisocyanate functional groups, polyurethanes, polyureas and polythioureas, respectively. As used herein, the term "poly-urethanes" encompasses these three types of polymers, for example, polyurethanes per se, polyureas and polythioureas, and also copolymers thereof.

A first type of compound involved in the preparation of the polyurethane of formula (IV) is a compound comprising at least one unit comprising at least one amine functional group. This compound may be multifunctional, but the compound may, for example, be difunctional, that is to say that, according to one embodiment disclosed herein, for example, this compound comprises two labile hydrogen atoms borne, for example, by a hydroxyl, primary amine, secondary amine or thiol functional group. A mixture of multifunctional and difunctional compounds in which the percentage of multifunctional compounds is low may also be used.

As mentioned above, this compound may comprise more than one unit comprising at least one functional group. In this case, it is a polymer bearing a repetition of the unit comprising at least one amine functional group.

Compounds of this type may be represented by one of the following formulae:

HZ-(P)$_n$-ZH or

HZ-(P')$_p$-ZH wherein Z, P, P', n and p are as defined above.

The compounds comprising at least one amine functional group may, for example, be chosen from N-methyldiethanolamine, N-tert-butyldiethanolamine and N-sulphoethyldiethanolamine.

The second compound involved in the preparation of the polyurethane of formula (IV) is a diisocyanate corresponding to the formula:

O=C=N—R$_4$—N=C=O wherein R$_4$ is as defined above.

For example, the second compound may be chosen from methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (IV) is a hydrophobic compound intended to form the terminal hydrophobic groups of the polymer of formula (IV).

This compound comprises at least one hydrophobic group and at least one functional group comprising labile hydrogen, for example at least one group chosen from hydroxyl, primary and secondary amine groups and thiol functional groups.

By way of example, this compound may be a fatty alcohol such as, stearyl alcohol, dodecyl alcohol or decyl alcohol. When this compound comprises a polymeric chain, it may be, for example, α-hydroxylated hydrogenated polybutadiene.

The hydrophobic groups of the polyurethane of formula (IV) may also result from the quaternization reaction of the tertiary amine of the compound comprising at least one tertiary amine unit. Thus, the hydrophobic groups can be introduced via the quaternizing agent. This quaternizing agent is a compound of the type RQ or R'Q, in which R and R', which may be identical or different, are as defined above and Q denotes a leaving group such as a halide, a sulphate, etc.

The cationic associative polyurethanes may also comprise a hydrophilic block. This block is provided by a fourth type of compound involved in the preparation of the polymer. This compound may be multifunctional. It may, for example, be difunctional. It is also possible to have a mixture in which the percentage of multifunctional compound is low.

The at least one functional group comprising labile hydrogen may, for example, be chosen from alcohol, primary and secondary amine and thiol functional groups. This compound may be a polymer terminated at the chain ends with at least one of these functional groups comprising labile hydrogen.

By way of example, when it is not a polymer, mention may be made of ethylene glycol, diethylene glycol and propylene glycol.

When it is a hydrophilic polymer, mention may be made, for example, of polyethers, sulphonated polyesters and sulphonated polyamides, or a mixture of these polymers. The hydrophilic compound may, for example, be a polyether and may, further, for example, be a poly(ethylene oxide) or poly(propylene oxide).

The hydrophilic group termed Y in formula (IV) is optional. Specifically, the units comprising quaternary amine or protonated functional groups may suffice to provide the solubility or water-dispersibility required for this type of polymer in an aqueous solution.

Although the presence of a hydrophilic group Y is optional, cationic associative polyurethanes comprising such a group may, for example, be used.

The cationic associative polyurethanes are water-soluble or water-dispersible.

The cationic poly(vinyllactam) polymers disclosed herein comprise:

a) at least one monomer chosen from vinyllactam and alkylvinyllactam monomers;

b) at least one monomer chosen from monomers of structure (V) and (VI) below:

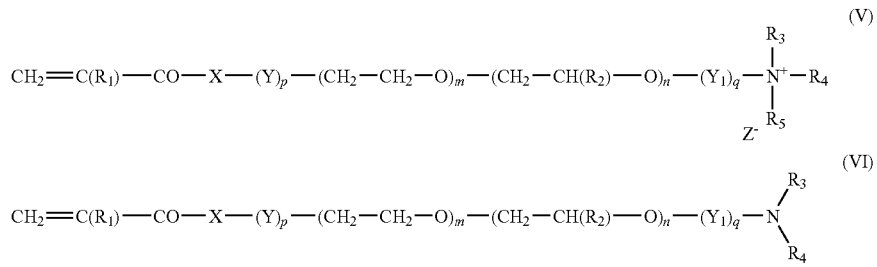

wherein:

X is chosen from an oxygen atom and radicals NR$_6$,

R$_1$ and R$_6$, which may be identical or different, are each chosen from a hydrogen atom and linear and branched C$_1$-C$_5$ alkyl radicals, R$_2$ is chosen from linear and branched C$_1$-C$_4$ alkyl radicals, R$_3$, R$_4$ and R$_5$, which may be identical or different, are each chosen from a hydrogen atom, linear and branched C$_1$-C$_{30}$ alkyl radicals and radicals of formula (VII):

—(Y$_2$)$_r$—(CH$_2$—CH(R$_7$)—O)$_x$—R$_8$  (VII)

Y, Y$_1$ and Y$_2$, which may be identical or different, are each chosen from linear and branched C$_2$-C$_{16}$ alkylene radicals, R$_7$ is chosen from a hydrogen atom, linear and branched C$_1$-C$_4$ alkyl radicals and linear and branched C$_1$-C$_4$ hydroxyalkyl radicals, R$_8$ is chosen from a hydrogen atom and linear and branched C$_1$-C$_{30}$ alkyl radicals, p, q and r, which may be identical or different, are each equal to either the value zero or the value 1, m and n, which may be identical or different, are each integers ranging from 0 to 100, x is an integer ranging from 1 to 100, Z is chosen from anions derived from organic or mineral acids, with the proviso that:
at least one of the substituents $R_3$, $R_4$, $R_5$ or $R_8$ is chosen from linear and branched $C_9$-$C_{30}$ alkyl radicals,
if m or n is not zero, then q is equal to 1, and
if m or n are equal to zero, then p or q is equal to 0.

The cationic poly(vinyllactam) polymers disclosed herein may be crosslinked or non-crosslinked, and may also be block polymers.

For example, the counter-ion Z of the monomers of formula (V) may be chosen from halide ions, phosphate ions, a methosulphate ion and a tosylate ion.

For example, $R_3$, $R_4$ and $R_5$, which may be identical or different, may each be chosen from a hydrogen atom and linear and branched $C_1$-$C_{30}$ alkyl radicals.

Further, for example, the monomer b) may be chosen from monomers of formula (IV) wherein, even further, for example, m and n are equal to zero.

The vinyllactam or alkylvinyllactam monomers may, for example, be chosen from compounds of structure (VIII):

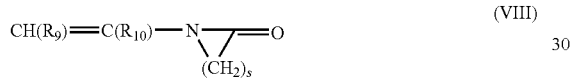

wherein:

s is an integer ranging from 3 to 6, $R_9$ is chosen from a hydrogen atom and $C_1$-$C_5$ alkyl radicals, and $R_{10}$ is chosen from a hydrogen atom and $C_1$-$C_5$ alkyl radicals, with the proviso that at least one of the radicals $R_9$ and $R_{10}$ is a hydrogen atom.

Further, for example, the monomer (VIII) may be a vinylpyrrolidone.

The cationic poly(vinyllactam) polymers disclosed herein may also comprise at least one additional monomer, which may, for example, be cationic or non-ionic.

As the at least one associative polymer that may be used in the composition disclosed herein, mention may be made of the following terpolymers comprising at least:

a)—a monomer of formula (VIII), b)—a monomer of formula (V) wherein p=1, q=0, $R_3$ and $R_4$, which may be identical or different, are each chosen from, a hydrogen atom and $C_1$-$C_5$ alkyl radicals and $R_5$ is chosen from $C_9$-$C_{24}$ alkyl radicals, and c)—a monomer of formula (VI) wherein $R_3$ and $R_4$, which may be identical or different, are each chosen from a hydrogen atom and $C_1$-$C_5$ alkyl radicals.

For example, terpolymers comprising, on a weight basis, 40% to 95% of monomer (a), 0.1% to 55% of monomer (c) and 0.25% to 50% of monomer (b) can be used.

Such polymers are described in Patent Application No. WO 00/68282, the content of which is hereby incorporated by reference.

Cationic poly(vinyllactam) polymers that can be used in the composition disclosed herein may, for example, be chosen from vinylpyrrolidone/dimethylaminopropylmethacrylamide/-dodecyldimethylmethacrylamidopropylammonium tosylate terpolymers, vinylpyrrolidone/dimethylaminopropylmethacrylamide/cocoyidimethylmethacrylamidopropyl ammonium tosylate terpolymers, vinylpyrrolidone/dimethylaminopropyl-methacrylamide/lauryidimethylmethacrylamidopropylammonium tosylate terpolymers, and vinylpyrrolidone/dimethylaminopropylmethacrylamide/lauryldimethylmethacrylamido-propylammonium chloride terpolymers.

The weight-average molecular mass of the cationic poly(vinyllactam) polymers disclosed herein may, for example, range from 500 to 20 000 000. Further, for example, it may range from 200 000 to 2 000 000 and even further, for example, from 400 000 to 800 000.

The cationic amphiphilic polymers disclosed herein may, for example, be chosen from acrylic terpolymers as described in Patent Application No. EP-1 090 623 and which comprise:

for example, from 5% to 80% by weight, further, for example, from 15% to 70% by weight and even further, for example, from 40% to 70% by weight of an acrylate monomer (a) chosen from $C_1$-$C_6$ alkyl acrylates and $C_1$-$C_6$ alkyl methacrylates;

for example, from 5% to 80% by weight further, for example, from 10% to 70% by weight and even further, for example, from 20% to 60% by weight, of a monomer (b) chosen from heterocyclic vinyl compounds comprising at least one atom chosen from nitrogen and sulphur atoms, (meth)acrylamides, mono- and di($C_1$-$C_4$)alkylamino($C_1$-$C_4$)alkyl (meth)acrylates, and mono- and di($C_1$-$C_4$)alkylamino($C_1$-$C_4$)alkyl(meth)acrylamides;

for example, from 0.1% to 30% by weight, further, for example, from 0.1% to 10% by weight, of a monomer (c) chosen from: (i) a urethane produced by reaction between a monoethylenic unsaturated isocyanate and a non-ionic surfactant with a $C_{1-4}$ alkoxy end; (ii) a block copolymer of 1,2-butylene oxide and of 1,2-ethylene oxide; (iii) a copolymerizable ethylenic unsaturated surfactant monomer obtained by condensation of a non-ionic surfactant with an α,β-ethylenic unsaturated carboxylic acid and the anhydride thereof; (iv) a surfactant monomer chosen from the products of reaction such as a urea of a monoethylenic unsaturated monoisocyanate with a non-ionic surfactant containing an amine functional group; (v) a (meth)allyl ether of formula $CH_2$=$CR_1CH_2OA_mB_nA_pR_2$ wherein $R_1$ is chosen from a hydrogen atom and a methyl group, A is chosen from propylenoxy and butylenoxy groups, B is an ethylenoxy group, n is equal to zero or is an integer less than or equal to 200 and, for example, less than 100, m and p, which may be identical or different, are each equal to zero or an integer less than n and $R_2$ is chosen from hydrophobic groups of at least 8 carbon atoms, for example, comprising from $C_8$-$C_{30}$ carbon atoms; and (vi) a non-ionic monomer of urethane produced by reaction of a monohydric non-ionic surfactant with a monoethylenic unsaturated isocyanate;

the weight percentages of monomers being based on the total weight of the monomers constituting the terpolymer.

Acrylate monomers (a) that may, for example, be used in the composition disclosed herein can comprise $C_2$-$C_6$ alkyl acrylates. Ethyl acrylate may, for example, be used.

Examples of monomers (b) which can be used in the composition disclosed herein are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylamino-propylacrylamide, N,N-dimethylamino-propylmethacrylamide, N,N-diethylaminopropylacrylamide and N,N-di-ethylaminopropylmethacrylamide. In one embodiment, N,N-dimethylaminoethyl methacrylate can be used.

The monomers (c) which can, for example, be used in the composition disclosed herein may be copolymerizable ethylenic unsaturated surfactant monomers obtained by condensing a non-ionic surfactant with an $\alpha,\beta$-ethylenic unsaturated carboxylic acid and the anhydride thereof, for example, $C_3$-$C_4$ mono- or dicarboxylic acids and the anhydrides thereof and further, for example, acrylic acid, methacrylic acid, crotonic acid, maleic acid, maleic anhydride and even further, for example, itaconic acid and itaconic anhydride.

The monomers (c) that can be used in the composition disclosed herein, for example, correspond to the copolymerizable ethylenic unsaturated surfactant monomers obtained by condensing a non-ionic surfactant with itaconic acid. Among the non-ionic surfactants which may be mentioned, for example, are $C_{10}$-$C_{30}$ fatty alcohols alkoxylated with 2 to 100 mol and, for example, from 5 to 50 mol of an alkylene oxide, such as, polyethylene glycol ethers of $C_{10}$-$C_{30}$ fatty alcohols and, for example, the polyethylene glycol ethers of cetyl alcohol which are called CETETH in the CTFA dictionary, 7th edition, 1997.

Acrylic terpolymers may thus be chosen from acrylic terpolymers comprising acrylates, amino(meth)acrylates and $C_{10}$-$C_{30}$ alkyl itaconate, polyoxyethylenated with 20 mol of ethylene oxide.

Conventional methods for preparing these acrylic terpolymers are known to those skilled in the art. Such methods include solution polymerization, precipitation polymerization and emulsion polymerization. Terpolymers used in the composition disclosed herein and methods for preparing them are described, for example, in Patent Application Nos. EP-A-0 824 914 and EP-A-0 825 200.

Among these terpolymers, the ASTRUCTURE7 PLUS polymer sold by the company National Starch, which comprises acrylates, amino(meth)acrylates and $C_{10}$-$C_{30}$ alkyl itaconate, polyoxyethylenated with 20 mol of ethylene oxide, in the form of an aqueous dispersion containing 20% active material can be used, for example.

In addition to these monomers, the terpolymers can comprise other monomers which allow the terpolymers to be crosslinked. These monomers can be used in relatively low proportions, of up to 2% by weight, relative to the total weight of the monomers used to prepare the terpolymers. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Crosslinking monomers may, for example, be chosen from, divinylbenzenes, trivinylbenzenes, 1,2,4-trivinylcyclohexene, 1,5-hexadiene, 1,5,9-decatriene, 1,9-deca-diene, 1,5-heptadiene, diallyl phthalates, ethylene glycol dimethacrylate, polyethylene glycol dimethacrylates, penta- and tetraacrylates, triallyl pentaerythritols, octaallyl sucroses, cycloparaffins, cycloolefins and N-methylenebisacrylamide.

Amphoteric Polymers

The at least one associative polymer disclosed herein may also be chosen from amphoteric associative polymers.

As used herein, the term "amphoteric polymers" means polymers which comprise units K and M randomly distributed in the polymer chain, wherein K is a unit derived from a monomer comprising at least one basic nitrogen atom and M is a unit deriving from an acidic monomer comprising at least one group chosen from carboxylic and sulphonic groups, or K and M, which may be identical or different, are each chosen from groups derived from zwitterionic carboxybetaine and sulphobetaine monomers;

K and M may also be chosen from cationic polymer chains comprising at least one group chosen from primary, secondary, tertiary and quaternary amine groups, wherein at least one of the amine groups bears at least one group chosen from carboxylic and sulphonic groups linked via a hydrocarbon-based radical, or K and M form part of a chain of a polymer comprising an $\alpha,\beta$-dicarboxylic ethylene unit in which one of the carboxylic groups has been made to react with a polyamine comprising at least one amine group chosen from primary and secondary amine groups.

The amphoteric polymers used in the composition disclosed herein may further comprise at least one fatty chain comprising from 8 to 30 carbon atoms, and may be chosen, for example, from polymers derived from polyaspartic acid and comprising at least one fatty chain comprising from 8 to 30 carbon atoms, such as those:

described and prepared in Patent Application No. EP 0 767 191, the content of which is hereby incorporated by reference. Such polymers are prepared in conventional manner by reacting polysuccinimide (PSI) with fatty-chain ($C_8$-$C_{24}$) amines in a solvent medium in the presence or absence of a basic catalyst such as, aliphatic tertiary amines, followed by amphoterization of the resultant product by reaction with a halogenated organic acid.

The $C_8$-$C_{24}$ fatty-chain amines which are reacted with the PSI, may, for example, be chosen from octylamine, nonylamine, decylamine, dodecylamine, tetradecylamine, hexadecylamine, octadecylamine, octadecenylamine, eicosyldecylamine, octynylamine, decenylamine, dedecenylamine, tetradecenylamine, hexadecenylamine, octadecenylamine and eicosenylamine.

Examples of such polymers are prepared by reacting PSI with n-laurylamine or with n-stearylamine in the presence of N,N-dimethyl-1,3-propanediamine as basic catalyst, followed by amphoterization of the resultant product by reaction with potassium monochloroacetate. These polymers are prepared with greater details on pages 13 to 20 (lines 1-4) and in Examples 1 to 5 on pages 28 to 34 (lines 1-4) of the Patent Application No. EP 0 767 191.

described and prepared in Patent Application No. EP 0 884 344, whose content is hereby incorporated by reference. Polymers of this kind are prepared by reacting gaseous ammonia with a $C_8$-$C_{24}$ alkyl or alkenyl monomaleate in a solvent medium under reduced pressure at a temperature of 120-140° C. for 4 to 6 hours.

The $C_8$-$C_{24}$ alkyl or alkenyl radicals may, for example, be chosen from the following linear or branched radicals: decyl, dodecyl, tetradecyl, hexadecyl, octadecyl and oleyl.

Examples of such polymers include polymers comprising aspartic acid units and decyl aspartate units, polymers comprising aspartic acid units and dodecyl aspartate units, polymers comprising aspartic acid units and cetyl aspartate units, polymers comprising aspartic acid units and stearyl aspartate units, and polymers comprising aspartic acid units and n-decylaspartamide-units, which are described in Examples 1 to 6 in Patent Application No. EP 0 884 344.

described and prepared in Patent Application No. EP 0 959 094, the content of which is hereby incorporated by reference. Polymers of this kind are prepared by reacting, in a solvent medium, gaseous ammonia with a maleic acid monoamide, polyoxy-alkylenated and hydrophobically modified by a linear or branched $C_8$-$C_{30}$ alkyl or alkenyl chain, optionally in a mixture with a monoester of maleic acid.

An example of a polymer thus prepared is described in Example 2 on page 11 of Patent Application No. EP 0 959 094.

described and prepared in Patent Application No. EP 0 959 090, the content of which is hereby incorporated by reference. Hydrophobically modified polymers of this kind of high molecular weight are obtained from derivatives of maleic acid and gaseous ammonia and difunctional or polyfunctional amines or alcohols.

Examples of copolymers comprising aspartic acid units and cetyl aspartate units or comprising aspartic acid units and cetyl aspartate units are given, respectively, in Examples 3 and 5 of Patent Application No. EP 0 959 090.

or else those described and prepared in Patent Application No. EP 0 959 091, the content of which is hereby incorporated by reference. Hydrophobically modified polymers of this kind are prepared from maleic acid monoester or monoamide and gaseous ammonia.

Examples of such copolymers are given in Examples 1, 2, 3 and 5 of Patent Application No. EP 0 959 091.

For example, as used herein the amphoteric polymers comprising at least one fatty chain comprising 8 to 30 carbon atoms are chosen from those comprising at least one non-cyclic cationic unit. For example, the polymers prepared from or comprising from 1 to 20 mol % of monomer comprising at least one fatty chain, further, for example, from 1.5 to 15 mol % and even further, for example, from 1.5 to 6 mol %, relative to the total number of moles of monomers.

The amphoteric polymers comprising at least one fatty chain that may be used in the composition disclosed herein comprise, or are prepared by copolymerizing.

1) at least one monomer chosen from monomers of formula (IXa) and (IXb):

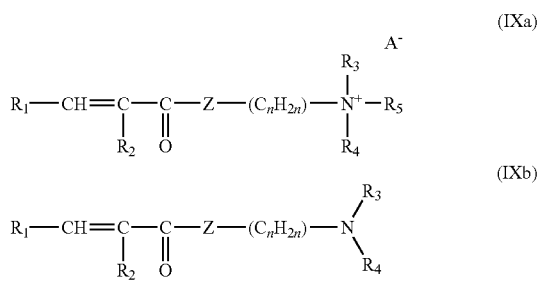

wherein $R_1$ and $R_2$, which may be identical or different, are each chosen from a hydrogen atom and a methyl radical, $R_3$, $R_4$ and $R_5$, which may be identical or different, are each chosen from linear and branched alkyl radicals comprising from 1 to 30 carbon atoms, Z is chosen from an NH group and an oxygen atom, n is an integer ranging from 2 to 5, and $A^-$ is chosen from anions derived from organic or mineral acids, such as a methosulphate anion or a halide such as chloride or bromide;

2) at least one monomer chosen from monomers of formula (X)

$$R_6\text{—}CH\text{=}CR_7\text{—}COOH \qquad (X)$$

wherein: $R_6$ and $R_7$, which may be identical or different, are each chosen from a hydrogen atom and a methyl radical; and 3) at least one monomer chosen from monomers of formula (XI):

$$R_6\text{—}CH\text{=}CR_7\text{—}COXR_8 \qquad (XI)$$

wherein $R_6$ and $R_7$, which may be identical or different, are each chosen from a hydrogen atom and a methyl radical, X is chosen from oxygen and nitrogen atoms and $R_8$ is chosen from linear and branched alkyl radicals comprising from 1 to 30 carbon atoms; at least one of the monomers of formula (IXa), (IXb) or (XI) comprising at least one fatty chain.

The monomers of formulae (IXa) and (IXb) may, for example, be chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulphate.

For example, the monomer of formula (IXa) can be chosen from acrylamidopropyltrimethylammonium chloride and methacrylamidopropyltrimethylammonium chloride.

The monomers of formula (X) may, for example, be chosen from acrylic acid, methacrylic acid, crotonic acid and 2-methylcrotonic acid. Further, for example, the monomer of formula (X) can be an acrylic acid.

The monomers of formula (XI) may, for example, be chosen from $C_{12}$-$C_{22}$ and, for example, $C_{16}$-$C_{18}$ alkyl acrylates and methacrylates.

The monomers constituting the amphoteric polymers comprising at least one fatty chain may, for example, be already neutralized and/or quaternized.

The ratio of the number of cationic charges/anionic charges may, for example, be equal to 1.

The amphoteric polymers comprising at least one fatty chain may comprise from 1 mol % to 10 mol % of the monomer comprising a fatty chain (monomer of formula (IXa), (IXb) or (XI)), and, for example, from 1.5 mol % to 6 mol %.

The weight-average molecular weights of the amphoteric polymers comprising at least one fatty chain may range from 500 to 50 000 000 and further, for example, from 10 000 to 5 000 000.

The amphoteric polymers comprising at least one fatty chain may also comprise other monomers, for example, non-ionic monomers, such as $C_1$-$C_4$ alkyl acrylates or methacrylates.

The amphoteric polymers comprising at least one fatty chain are described and prepared, for example, in Patent Application No. WO 98/44012.

The amphoteric polymers comprising at least one fatty chain may, for example, be chosen from acrylic acid/(meth)acrylamidopropyltrimethylammonium chloride/stearyl methacrylate terpolymers.

In one embodiment, the oxidation dyeing composition disclosed herein comprises at least one associative polymer chosen from cationic and non-ionic polymers comprising at least one fatty chain. In another embodiment, the composition disclosed herein comprises cationic polymers comprising at least one fatty chain. For example, the at least one associative polymer may be chosen from cationic polyurethanes.

The at least one associative polymer may be present in the composition, for example, in an amount ranging from 0.05% to 10% by weight, relative to the total weight of the composition and further, for example, from 0.1% to 5% by weight, relative to the total weight of the composition.

The ratio by weight of the at least one $C_{14}$-$C_{30}$ alkylsulphate to the at least one associative polymer ranges, for example, from 0.1:1 to 10:1, and further, for example, from 0.5:1 to 5:1.

Fatty Alcohols

The at least one fatty alcohol disclosed herein may, for example, be chosen from non-oxyalkylenated and non-glycerolated, linear and branched, saturated and unsaturated fatty alcohols and comprise from 8 to 40 carbon atoms. For example, the at least one fatty alcohol may be chosen from cetyl alcohol, stearyl alcohol and oleyl alcohol.

In one embodiment, the fatty alcohol may be chosen from oxyalkylenated and glycerolated fatty alcohols.

As used herein, the term "oxyalkylenated fatty alcohols" means any pure fatty alcohol of the following structure:

$$RO\text{---}(Z)_m\text{---}H$$

wherein:

R is chosen from saturated and unsaturated, linear and branched radicals comprising from 8 to 40 carbon atoms, for example, from 8 to 30 carbon atoms, Z is chosen from oxyethylenated (i) and/or oxypropylenated (ii)$_1$ and (ii)$_2$ radicals of the following respective formulae:

$$\text{---}CH_2\text{---}CH_2\text{---}O\text{---} \quad (i)$$

$$\text{---}CH_2\text{---}CH\text{---}O\text{---} \quad (ii)_1$$
$$\quad\quad\quad |$$
$$\quad\quad\quad CH_3$$

$$\text{---}CH_2\text{---}CH_2\text{---}CH_2\text{---}O\text{---} \quad (ii)_2$$

m represents the number of ethylene oxide (i) and/or propylene oxide (ii)$_1$ or (ii)$_2$ groups, ranging, for example, from 1 to 250 and further, for example, from 2 to 100.

As used herein, the term "glycerolated fatty alcohols" means any pure fatty alcohol of the following structure:

$$RO\text{---}(Z)_n\text{---}H$$

wherein:

R is chosen from saturated and unsaturated, linear and branched radicals comprising, for example, from 8 to 40 carbon atoms and further, for example, from 8 to 30 carbon atoms, Z is chosen from glycerolated radicals (iii) of the following formula:

$$\text{---}CH_2\text{---}CH\text{---}O\text{---} \quad (iii)$$
$$\quad\quad\quad |$$
$$\quad\quad\quad CH_2OH$$

n represents the number of glycerol groups (iii) and ranges, for example, from 1 to 30 and further, for example, from 1 to 10.

For example, the oxyalkylenated fatty alcohols may be chosen from saturated and unsaturated, linear and branched fatty alcohols comprising from 10 to 20 carbon atoms and from 2 to 40 ethylene oxide groups. The oxyalkylenated fatty alcohol compounds may, for example, be chosen from the following commercialized products:

MERGITAL LM2 (Cognis) [lauryl alcohol 2 EO];

IFRALAN L12 (Ifrachem) and REWOPAL 12 (Goldschmidt) [lauryl alcohol 12 EO];

EMPILAN KA 2.5/90FL (Albright & Wilson) and MERGITAL BL309 (Cognis) [decyl alcohol 3 EO];

EMPILAN KA 5/90 FL (Albright & Wilson) and MERGITAL BL589 (Cognis) [decyl alcohol 5 EO];

BRIJ 58 (Uniqema) and SIMULSOL 58 (Seppic) [cetyl alcohol 20 EO];

EMULGIN 05 (Cognis) [oleocetyl alcohol 5 EO];

MERGITAL OC30 (Cognis) [oleocetyl alcohol 30 EO];

BRIJ 72 (Uniqema) [stearyl alcohol 2 EO];

BRIJ 76 (Uniqema) [stearyl alcohol 10 EO];

BRIJ 78P (Uniqema) [stearyl alcohol 20 EO];

BRIJ 700 (Uniqema) [stearyl alcohol 100 EO];

EMULGIN B1 (Cognis) [cetylstearyl alcohol 12 EO];

EMULGIN L (Cognis) [cetyl alcohol 9 EO and 2 PO]; and

WITCONOL APM (Goldschmidt) [myristyl alcohol 3 PO].

The glycerolated fatty alcohol compounds may, for example, be chosen from lauryl alcohol containing 4 mol of glycerol (INPCI name: Polyglyceryl-4 lauryl ether), oleyl alcohol containing 4 moles of glycerol (INPCI name: Polyglyceryl-4 oleyl ether), oleyl alcohol containing 2 mol of glycerol (INPCI name: Polyglyceryl-2 oleyl ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The at least one fatty alcohol may represent a mixture of fatty alcohols, which means that in a commercial product a plurality of species of fatty alcohols may coexist in the form of a mixture.

The at least one fatty alcohol is present in the composition in an amount ranging, for example, from 0.05% to 30% by weight, relative to the total weight of the composition and further, for example, from 0.5% to 20% by weight, relative to the total weight of the composition.

Oxidation Dyes

The at least one oxidation dye that may be used in the composition disclosed herein may, for example, be chosen from oxidation bases and couplers.

In one embodiment, the composition disclosed herein comprises at least one oxidation base.

The oxidation bases that may be used in the composition disclosed herein may, for example, be chosen from those conventionally used in oxidation dyeing, for example, ortho- and para-phenylenediamines, double bases, ortho- and para-aminophenols, heterocyclic bases, and the acid addition salts thereof.

For example, the oxidation bases may be chosen from:

(I) para-phenylenediamines of formula (XII) below, and the acid addition salts thereof:

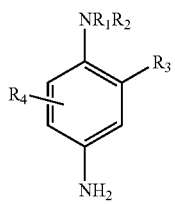

(XII)

wherein:
- $R_1$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals and $C_1$-$C_4$ alkyl radicals substituted with at least one group chosen from nitrogenous, phenyl and 4'-aminophenyl groups;
- $R_2$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals and $C_1$-$C_4$ alkyl radicals substituted with at least one nitrogenous group;
- $R_1$ and $R_2$ may also form, together with the nitrogen atom that bears them, at least one heterocycle chosen from 5- and 6-membered nitrogen heterocycles optionally substituted with at least one group chosen from alkyl, hydroxyl and ureido groups;
- $R_3$ is chosen from a hydrogen atom, halogen atoms such as a chlorine atom, $C_1$-$C_4$ alkyl radicals, sulpho radicals, carboxyl radicals, $C_1$-$C_4$ monohydroxyalkyl radicals, $C_1$-$C_4$ hydroxyalkoxy radicals, acetylamino($C_1$-$C_4$)alkoxy radicals, mesylamino($C_1$-$C_4$)alkoxy radicals and carbamoylamino ($C_1$-$C_4$)alkoxy radicals, and
- $R_4$ is chosen from a hydrogen atom, halogen atoms, and $C_1$-$C_4$ alkyl radicals.

The nitrogenous groups of formula (XII) above may, for example, be chosen from amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium and ammonium radicals.

The para-phenylenediamines of formula (XII) may, for example, be chosen from para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid addition salts thereof.

The para-phenylenediamines of formula (XII) may also, for example, be chosen from para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid addition salts thereof (II) As used herein, the term "double bases" means compounds comprising at least two aromatic nuclei bearing at least one group chosen from amino and hydroxyl groups.

The double bases that can be used as oxidation bases in the dye composition disclosed herein may, for example, be chosen from compounds corresponding to formula (XIII) below, and the acid addition salts thereof:

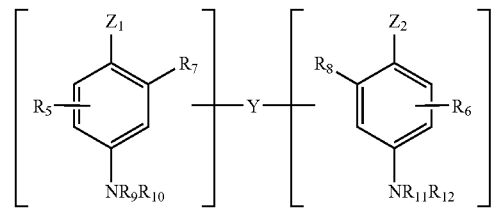

(XIII)

wherein:
- $Z_1$ and $Z_2$, which may be identical or different, are each chosen from a hydroxyl radical and an —$NH_2$ radical which may be substituted with at least one entity chosen from $C_1$-$C_4$ alkyl radicals and a linking arm Y;
- the linking arm Y is chosen from linear and branched alkylene chains comprising from 1 to 14 carbon atoms, which may be interrupted by or terminated with at least one entity chosen from nitrogenous groups and heteroatoms such as oxygen, sulphur and nitrogen atoms, and optionally substituted with at least one radical chosen from hydroxyl and $C_1$-$C_6$ alkoxy radicals;
- $R_5$ and $R_6$, which may be identical or different, are each chosen from a hydrogen atom and halogen atoms, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and a linking arm Y; and
- $R_7$, $R_8$, $R_9$, $R_{10}$, $R_{11}$ and $R_{12}$, which may be identical or different, are each chosen from a hydrogen atom, a linking arm Y and $C_1$-$C_4$ alkyl radicals;

with the overall proviso that the compounds of formula (XIII) comprise only one linking arm Y per molecule.

The nitrogenous groups of formula (XIII) above may, for example, be chosen from amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium and ammonium radicals.

The double bases of formula (XIII) above may, for example, be chosen from N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Further, for example, the double bases of formula (XIII) may be chosen from N,N'-bis(β-hydroxyethyl)-N,N'-bis(4'- aminophenyl)-1,3-diaminopropanol and 1,8-bis(2,5-diaminophenoxy)-3,5-dioxaoctane, and the acid addition salts thereof.

(III) the para-aminophenols corresponding to formula (XIV) below, and the acid addition salts thereof:

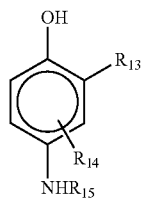

(XIV)

wherein:

$R_{13}$ is chosen from a hydrogen atom, halogen atoms such as fluorine $C_1$-$C_4$ alkyl, $C_1$-$C_4$ monohydroxyalkyl, ($C_1$-$C_4$) alkoxy($C_1$-$C_4$)alkyl, $C_1$-$C_4$ aminoalkyl and hydroxy($C_1$-$C_4$)alkylamino($C_1$-$C_4$)alkyl radicals;

$R_{14}$ is chosen from a hydrogen atom, halogen atoms such as fluorine, and $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl and ($C_1$-$C_4$)alkoxy-($C_1$-$C_4$)alkyl radicals; and $R_{15}$ is chosen from a hydrogen atom and $C_1$-$C_4$ alkyl radicals.

The para-aminophenols of formula (XIV) above may, for example, be chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol and the acid addition salts thereof.

(IV) the ortho-aminophenols that can be used as oxidation bases in the composition disclosed herein may, for example, be chosen from 2-aminophenol, 2-amino-1-hydroxy-5-methylbenzene, 2-amino-1-hydroxy-6-methylbenzene and 5-acetamido-2-aminophenol, and the acid addition salts thereof.

(V) the heterocyclic bases that can be used as oxidation bases in the dye composition disclosed herein, may, for example, be chosen from pyridine derivatives, pyrimidine derivatives and pyrazole derivatives, and the acid addition salts thereof.

The pyridine derivatives may be chosen from compounds described, for example, in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

The pyrimidine derivatives may be chosen from the compounds described, for example, in German Patent No. DE 2 359 399 and Japanese Patent Nos. JP 88-169 571 and JP 91-10659 and Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives which may be chosen, for example, from those disclosed in Patent Application No. FR-A-2 750 048, such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol-3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylamino-pyrazolo-[1,5-a]pyrimidine and the addition salts thereof and the tautomeric forms thereof, when a tautomeric equilibrium exists.

The pyrazole derivatives may, for example, be chosen from compounds described in Patent Nos. DE 3 843 892, DE 4 133 957 and Patent Application Nos. WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The oxidation bases may be present in the composition disclosed herein in an amount ranging from 0.0005% to 12% by weight, relative to the total weight of the composition, and further, for example, from 0.005% to 8% by weight, relative to the total weight of the composition.

The couplers that may be used in the composition disclosed herein may, for example, be chosen from those conventionally used in oxidation dye compositions, such as meta-aminophenols, meta-phenylenediamines and meta-diphenols, naphthols, and heterocyclic couplers such as indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

These couplers may, for example, be chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the acid addition salts thereof.

The couplers may, for example, be present in an amount ranging from 0.0001% to 10% by weight, relative to the total weight of the composition, and further, for example, from 0.005% to 5% by weight, relative to the total weight of the composition.

The acid addition salts of the oxidation bases and couplers may be chosen, for example, from hydrochlorides, hydrobromides, sulphates, tartrates, lactates and acetates.

Direct Dyes

The composition disclosed herein may also comprise at least one direct dye, in addition to the at least one oxidation dye defined above, in order to enrich the shades with glints. The at least one direct dye may, for example, be chosen from neutral, cationic and anionic nitro dyes, azo dyes and anthraquinone dyes, in an amount ranging, for example, from 0.001% to 20% by weight, relative to the total weight of the composition and further, for example, from 0.01% to 10% by weight, relative to the total weight of the composition.

Additional Polymers

The at least one composition (A) and/or at least one composition (B) may further comprise, for example, at least one additional polymer chosen from cationic and amphoteric substantive polymers different from the at least one associative polymer disclosed above.

Cationic Substantive Polymers

As used herein, the term "cationic polymer" means any polymer comprising at least one group chosen from cationic groups and groups that may be ionized into cationic groups.

The cationic substantive polymers that may be used in the composition disclosed herein may, for example, be chosen from all those already known per se as improving the cosmetic properties of the hair, i.e. for example, those polymers described in Patent Application No. EP-A-337 354 and in French Patent Nos. FR-2 270 846, 2 383 660, 2 598 611, 2 470 596 and 2 519 863.

The cationic substantive polymers may, for example, be chosen from those polymers comprising units comprising at least one group chosen from primary, secondary, tertiary and quaternary amine groups, which may either form part of the main polymer chain or may be borne by a side substituent directly attached thereto.

The cationic substantive polymers may, for example, have a number-average molecular mass ranging from 500 to $5 \times 10^6$ and further, for example, ranging from $10^3$ to $3 \times 10^6$.

The cationic substantive polymers may, for example, be chosen from polyamine, polyamino amide and polyquaternary ammonium polymers.

These are known products. They are described, for example, in French Patents Nos. 2 505 348 and 2 542 997. For example, the cationic substantive polymers may be chosen from:

(1) homopolymers or copolymers derived from acrylic or methacrylic esters or amides and comprising at least one of the units of formula (XV), (XVI), (XVII) or (XVIII) below:

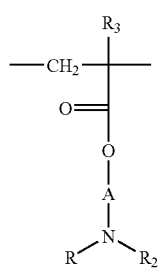

(XV)

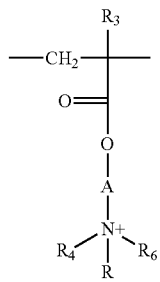

(XVI)

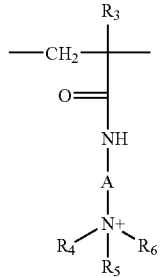

(XVII)

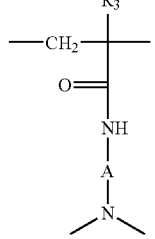

(XVIII)

wherein:

$R_1$ and $R_2$, which may be identical or different, are each chosen from a hydrogen atom and alkyl groups comprising from 1 to 6 carbon atoms, for example, methyl and ethyl groups;

$R_3$, which may be identical or different, is chosen from a hydrogen atom and a $CH_3$ radical;

A, which may be identical or different, is chosen from linear and branched alkyl groups comprising from 1 to 6 carbon atoms, such as 2 or 3 carbon atoms, and hydroxyalkyl groups comprising from 1 to 4 carbon atoms;

$R_4$, $R_5$ and $R_6$, which may be identical or different, are each chosen from alkyl groups comprising from 1 to 6 carbon atoms; and X is chosen from anions derived from an inorganic or organic acid, such as a methosulphate anion or an anion chosen from halides such as chloride or bromide.

The polymers of family (1) can also contain at least one unit derived from comonomers, which may be chosen from the family of acrylamides, methacrylamides, diacetone acrylamides, acrylamides and methacrylamides substituted on the nitrogen with lower ($C_1$-$C_4$) alkyls, acrylic acids, methacrylic acids, acrylic esters, methacrylic esters, vinyllactams such as vinylpyrrolidone and vinylcaprolactam, and vinyl esters.

Thus, the polymers of family (1) may, for example, be chosen from:

copolymers of acrylamide and of dimethylaminoethyl methacrylate quaternized with dimethyl sulphate or with a dimethyl halide, such as the product sold under the name HERCOFLOC by the company Hercules, the copolymers of acrylamide and of methacryloyloxyethyltrimethylammonium chloride described, for example, in Patent Application No. EP-A-080 976 and sold under the name BINA QUAT P 100 by the company Ciba Geigy, the copolymer of acrylamide and of methacryloyloxyethyltrimethylammonium methosulphate sold under the name RETEN by the company Hercules, quaternized or non-quaternized vinylpyrrolidone/dialkylaminoalkyl acrylate or methacrylate copolymers, such as the products sold under the name "GAFQUAT" by the company ISP, for example, "GAFQUAT 734" or "GAFQUAT 755", or alternatively the products known as "COPOLYMER 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, and quaternized vinylpyrrolidone/dimethylaminopropylmethacrylamide copolymers such as the product sold under the name "GAFQUAT HS 100" by the company ISP.

(2) The cellulose ether derivatives comprising quaternary ammonium groups, described in French Patent No. 1 492 597, and, for example, the polymers sold under the names "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble monomer of quaternary ammonium, and described, for example, in U.S. Pat. No. 4,131,576, such as hydroxyalkylcelluloses, for example, hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

The commercial products corresponding to this definition are, for example, the products sold under the names "CELQUAT L 200" and "CELQUAT H 100" by the company National Starch.

(4) The cationic polysaccharides described, for example, in U.S. Pat. Nos. 3,589,578 and 4,031,307, such as guar gums comprising cationic trialkylammonium groups. Guar gums modified with a salt (e.g., chloride) of 2,3-epoxypropyltrimethylammonium may be used, for example.

Such products are sold, for example, under the trade names JAGUAR CL 3 S, JAGUAR C 15, JAGUAR C 17 or JAGUAR C162 by the company Meyhall.

(5) Polymers comprising piperazinyl units and divalent alkylene or hydroxyalkylene radicals comprising straight or branched chains, optionally interrupted by at least one entity chosen from oxygen, sulphur and nitrogen atoms and aromatic and heterocyclic rings and the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise at least one tertiary amine functional group, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. For example, these deriviatives may be chosen from adipic acid/dialkylaminohydroxyalkyldialkylenetriamine polymers wherein the alkyl radical comprises from 1 to 4 carbon atoms, such as methyl, ethyl and propyl. Such polymers are described, for example, in French Patent No. 1 583 363.

These derivatives may further, for example, be chosen from adipic acid/dimethylaminohydroxypropyl/diethylenetriamine polymers sold under the name "CARTARETINE F, F4 or F8" by the company Sandoz.

(8) The polymers obtained by reaction of a polyalkylene polyamine comprising two primary amine groups and at least one secondary amine group with a dicarboxylic acid chosen from diglycolic acids and saturated aliphatic dicarboxylic acids comprising from 3 to 6 carbon atoms. The molar ratio between the polyalkylene polyamine and the dicarboxylic acid may range, for example, from 0.8:1 and 1.4:1; the polyamino amide resulting therefrom may be reacted with epichlorohydrin in a molar ratio of epichlorohydrin relative to the secondary amine group of the polyamino amide ranging, for example, from 0.5:1 and 1.8:1. Such polymers are described, for example, in U.S. Pat. Nos. 3,227,615 and 2,961,347.

Polymers of this type are sold, for example, under the name "HERCOSETT 57" by the company Hercules Inc. or alternatively under the name "PD 170" or "DELSETTE 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers comprising, as the main constituent of the chain, at least one unit corresponding to formula (XIX) or (XX):

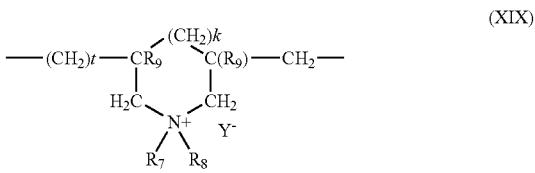

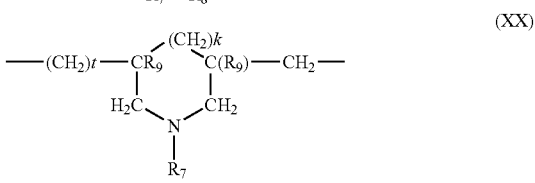

wherein:
k and t are equal to 0 or 1, the sum k+t being equal to 1;
$R_9$ is chosen from a hydrogen atom and a methyl radical;
$R_7$ and $R_8$, which may be identical or different, are each chosen from alkyl groups comprising from 1 to 6 carbon atoms, hydroxyalkyl groups in which the alkyl group, for example, comprises from 1 to 5 carbon atoms, and lower $C_1$-$C_4$ amidoalkyl group, or $R_7$ and $R_8$ can form, together with the nitrogen atom to which they are attached, heterocyclic groups such as piperidyl or morpholinyl; $R_7$ and $R_8$, which may be identical or different, can each, for example, be chosen from alkyl groups comprising from 1 to 4 carbon atoms; and
$Y^-$ is an anion such as bromide, chloride, acetate, borate, citrate, tartrate, bisulphate, bisulphite, sulphate or phosphate.

These polymers are described, for example, in French Patent No. 2 080 759 and in its Certificate of Addition 2 190 406.

Among the polymers defined above, mention may be made, for example, of the dimethyldiallylammonium chloride homopolymer sold under the name "MERQUAT 100" by the company Calgon (and its homologues of low weight-average molecular mass) and the copolymers of diallyldimethylammonium chloride and of acrylamide, sold under the name "MERQUAT 550".

(10) The quaternary diammonium polymers comprising repeating units corresponding to the formula below:

(XXI)

wherein:
$R_{10}$, $R_{11}$, $R_{12}$ and $R_{13}$, which may be identical or different, are each chosen from aliphatic, alicyclic and arylaliphatic radicals comprising from 1 to 6 carbon atoms and from lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally comprising a second heteroatom other than nitrogen, or alternatively $R_{10}$, $R_{11}$, $R_{12}$ and $R_{13}$, which may be identical or different, are each chosen from linear and branched $C_1$-$C_6$ alkyl radicals substituted with at least one group chosen from nitrile, ester, acyl and amide groups and groups —CO—O—$R_{14}$-D and —CO—NH—$R_{14}$-D wherein $R_{14}$ is chosen from alkylene groups and D is chosen from quaternary ammonium groups;

$A_1$ and $B_1$, which may be identical or different, are each chosen from linear and branched, saturated and unsaturated polymethylene groups comprising from 2 to 6 carbon atoms. The polymethylene groups may comprise, linked to or intercalated in the main chain, at least one entity chosen from aromatic rings, oxygen and sulphur atoms and sulphoxide, sulphone, disulphide, amino, alkylamino, hydroxyl, quaternary ammonium, ureido, amide and ester groups, and $X^-$ is chosen from anions derived from inorganic or organic acids;

$A_1$, $R_{10}$ and $R_{12}$ can form, with the two nitrogen atoms to which they are attached, a piperazine ring; in addition, if $A_1$ is chosen from linear and branched, saturated and unsaturated alkylene and hydroxyalkylene radicals, B can also be chosen from groups —$(CH_2)_n$—CO-D-OC—$(CH_2)_n$— wherein n ranges from 1 to 100, such as from 1 and 50, and D is chosen from:
a) a glycol residue of formula: —O-Z-O—, wherein Z is chosen from linear and branched hydrocarbon-based radicals and groups corresponding to one of the following formulae:

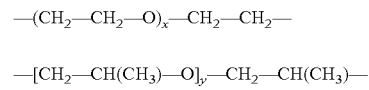

wherein x and y, which may be identical or different, are each integers ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon-based radicals, and the divalent radical

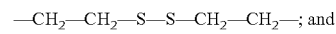

d) a ureylene group of formula: —NH—CO—NH—.

For example, $X^-$ can be an anion such as chloride or bromide.

These polymers may have a number-average molecular mass ranging from 1000 to 100 000.

These polymers are described, for example, in French Patent Nos. 2 320 330, 2 270 846, 2 316 271, 2 336 434 and 2 413 907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, the polymers can comprise repeating units corresponding to the following formula (XXII):

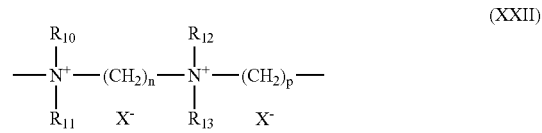

(XXII)

wherein:
$R_{10}$, $R_{11}$, $R_{12}$ and $R_{13}$, which may be identical or different, are each chosen from alkyl and hydroxyalkyl radicals comprising from 1 to 4 carbon atoms, n and p, which may be identical or different, are integers ranging from 2 to 20, and $X^-$ is an anion chosen from anions derived from inorganic or organic acids.

(11) Polyquaternary ammonium polymers comprising repeating units of formula (XXIII):

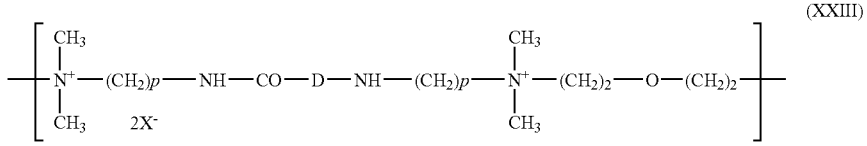

wherein:

p is an integer ranging from 1 to 6,

D may be zero or may be chosen from groups —$(CH_2)_r$—CO— wherein r is a number equal to 4 or 7, and $X^-$ is chosen from anions derived from an organic or inorganic acid.

The cationic polymers comprising units of formula (XXIII) are described, for example, in Patent Application No. EP-A-1 22 324 and can be prepared by the processes described in U.S. Pat. Nos. 4,157,388, 4,390,689, 4,702,906 and 4,719,282.

Polymers having a molecular mass, measured by carbon 13 NMR, of less than 100 000, and in whose formula:

p is 3, and a) D is group —$(CH_2)_4$—CO—, X is a chlorine atom, the molecular mass measured by carbon 13 NMR ($^{13}C$ NMR) being about 5600; a polymer of this type is proposed by the company Miranol under the name MIRAPOL-AD1, b) D is a group —$(CH_2)_7$—CO—, X is a chlorine atom, the molecular mass measured by carbon 13 NMR ($^{13}C$ NMR) being about 8100; a polymer of this type is proposed by the company Miranol under the name MIRAPOL-AZ1, c) D is equal to the value zero, X is a chlorine atom, the molecular mass measured by carbon 13 NMR ($^{13}C$ NMR) being about 25 500; a polymer of this type is sold by the company Miranol under the name MIRAPOL-A15, d) a block copolymer formed of units corresponding to the polymers described in paragraphs a) and c), proposed by the company Miranol under the names MIRAPOL-9 ($^{13}C$ NMR molecular mass about 7800), MIRAPOL-175 ($^{13}C$ NMR molecular mass about 8000) and MIRAPOL-95 ($^{13}C$ NMR molecular mass about 12 500).

For example, polymers with units of formula (XXIII) in which p is 3, D has the value zero, and X is a chlorine atom, the molecular mass measured by carbon 13 NMR ($^{13}C$ NMR) being about 25 500 can also be used in the compositions disclosed herein.

(12) Quaternary polymers of vinylpyrrolidone and of vinylimidazole, for example, the products sold under the names LUVIQUAT FC 905, FC 550 and FC 370 by the company BASF.

(13) Polyamines such as POLYQUART H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo or copolymerization being followed by crosslinking with a compound comprising olefinic unsaturation, for example, methylenebisacrylamide. In one embodiment, a crosslinked acrylamide/methacryloyloxyethyltrimethylammonium chloride copolymer (20/80 by weight) in the form of a dispersion comprising 50% by weight of the copolymer in mineral oil can be used. This dispersion is sold under the name "SALCARE® SC 92" by the company Allied Colloids. A crosslinked methacryloyloxyethyltrimethylammonium chloride homopolymer comprising 50% by weight of the homopolymer in mineral oil or in a liquid ester can also be used. These dispersions are sold under the names "SALCARE® SC 95" and "SALCARE® SC 96" by the company Allied Colloids.

Other cationic polymers which can be used in the composition disclosed herein are polyalkyleneimines, for example, polyethyleneimines, polymers comprising vinylpyridine or vinylpyridinium units, condensates of polyamines and of epichlorohydrin, quaternary polyureylenes and chitin derivatives.

Among all the cationic polymers which may be used in the composition disclosed herein, the polymers of families (1), (9), (10), (11), (12) and (14) may, for example, be used and even further, the polymers comprising repeating units of formulae (XXIV) and (XXV) below can also be used:

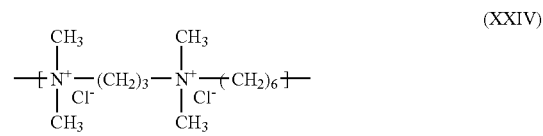

and, for example, those polymers whose molecular weight, determined by gel permeation chromatography, ranges from 9500 to 9900;

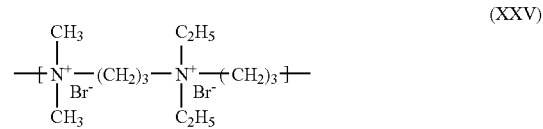

and, for example, those polymers whose molecular weight, determined by gel permeation chromatography, is about 1200.

The cationic substantive polymers may be present in the composition disclosed herein in an amount ranging, for example, from 0.01% to 10% by weight, relative to the total weight of the composition, further, for example, from 0.05% to 5% by weight, relative to the total weight of the composition, and even further, for example, from 0.1% to 3% by weight, relative to the total weight of the composition.

Amphoteric Substantive Polymers

The amphoteric substantive polymers that may be used in the composition disclosed herein may be chosen from polymers comprising units K and M randomly distributed in the polymer chain, wherein K is chosen from units derived from a monomer comprising at least one basic nitrogen atom and M is chosen from units derived from an acidic monomer comprising at least one group chosen from carboxylic and sulphonic groups, or alternatively K and M, which may be identical or different, are each chosen from groups derived from zwitterionic carboxybetaine and sulphobetaine monomers; K and M, which may be identical or different, are each chosen from cationic polymer chains comprising at least one group chosen from primary, secondary, tertiary and quaternary amine groups, wherein at least one of the amine groups bears a carboxylic or sulphonic group linked via a hydrocarbon-based radical, or alternatively K and M form part of a chain of a polymer comprising an α,β-dicarboxylic ethylene unit in which one of the carboxylic groups has been made to react with a polyamine comprising at least one amine group chosen from primary and secondary amine groups.

The amphoteric polymers corresponding to the above definition may, for example, be chosen from the following polymers:

(1) polymers resulting from the copolymerization of a monomer derived from a vinyl compound bearing at least one carboxylic group such as, acrylic acid, methacrylic acid, maleic acid, α-chloroacrylic acid, and a monomer derived from a substituted vinyl compound comprising at least one basic atom, such as, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer sold under the name POLYQUART KE 3033 by the company Henkel.

The substituted vinyl compound comprising at least one basic atom may also be a dialkyldiallylammonium salt such as dimethyldiallylammonium chloride. The copolymers of acrylic acid and of the latter monomer are proposed under the names MERQUAT 280, MERQUAT 295 and MERQUAT Plus 3330 by the company Calgon.

(2) Polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which can be used in the composition disclosed herein are groups in which the alkyl radicals comprise from 2 to 6 carbon atoms, for example, N-ethylacrylamide, N-tert-butylacrylamide, and the corresponding methacrylamides.

The acidic comonomers are chosen, for example, from acrylic acid, methacrylic acid, crotonic acid, itaconic acid, maleic acid and fumaric acid and alkyl monoesters, comprising from 1 to 4 carbon atoms, of maleic or fumaric acids or anhydrides.

For example, the basic comonomers may be chosen from aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name AMPHOMER or LOVOCRYL 47 by the company National Starch can, for example, be used.

(3) Crosslinked and alkylated polyamino amides partially or totally derived from polyamino amides of general formula:

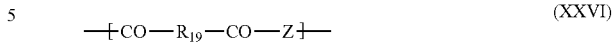

(XXVI)

wherein: $R_{19}$ is chosen from divalent radicals derived from saturated dicarboxylic acids, mono- and dicarboxylic aliphatic acids comprising an ethylenic double bond, esters of a lower alkanol comprising from 1 to 6 carbon atoms with these acids or radicals derived from the addition of any one of these acids to a bis(primary) or bis(secondary) amine, and Z is chosen from bis(primary), mono- and bis(secondary) polyalkylene-polyamine radicals and, for example, represents:

a) in proportions ranging from 60 to 100 mol %, the radical

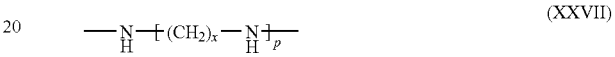

(XXVII)

wherein x=2 and p=2 or 3, or alternatively x=3 and p=2 this radical being derived from diethylenetriamine, from triethylenetetraamine or from dipropylenetriamine;

b) in proportions ranging from 0 to 40 mol %, the radical (XXVII) above wherein x=2 and p=1 and is derived from ethylenediamine, or the radical deriving from piperazine:

c) in proportions ranging from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids may, for example, be chosen from acids comprising from 6 to 10 carbon atoms, such as adipic acid, 2,2,4-trimethyladipic acid and 2,4,4-trimethyladipic acid, terephthalic acid and acids comprising an ethylenic double bond such as, acrylic acid, methacrylic acid and itaconic acid.

The alkane sultones used in the alkylation may, for example, be chosen from propane sultone and butane sultone, and the salts of the alkylating agents may, for example, be chosen from sodium and potassium salts.

(4) Polymers comprising zwitterionic units of formula:

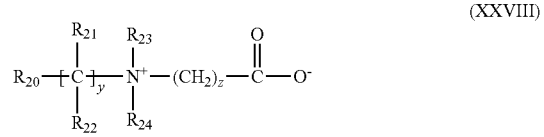

(XXVIII)

wherein $R_{20}$ is a polymerizable unsaturated group chosen from acrylate, methacrylate, acrylamide and methacrylamide groups, y and z, which may be identical or different, are each integers ranging from 1 to 3, $R_{21}$ and $R_{22}$, which may be identical or different, are each chosen from a hydrogen atom, and methyl, ethyl and propyl groups, $R_{23}$ and $R_{24}$, which may be identical or different, are each chosen from a hydrogen atom and alkyl radicals such that the sum of the carbon atoms in $R_{23}$ and $R_{24}$ does not exceed 10.

The polymers comprising such units can also comprise units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethylcarboxymethylammonioethyl methacrylate such as the product sold under the name DIAFORMER Z301 by the company Sandoz.

(5) Polymers derived from chitosan, described, for example, French Patent No. 2137684 or U.S. Pat. No. 3,879,376, comprising together in their chain monomer units corresponding to formulae (XXIX), (XXX) and (XXXI) below:

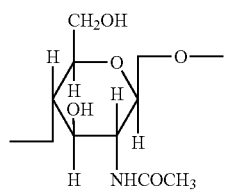

(XXIX)

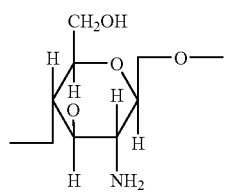

(XXX)

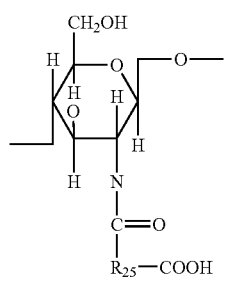

(XXXI)

the unit (XXIX) being present in proportions ranging from 0 to 30%, the unit (XXX) in proportions ranging from 5 to 50% and the unit (XXXI) in proportions ranging from 30 to 90%, it being understood that, in this unit (XXXI), $R_{25}$ is chosen from radicals of formula:

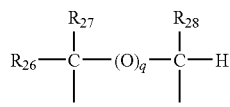

wherein q is equal to zero or 1;

if q=0, $R_{26}$, $R_{27}$ and $R_{28}$, which may be identical or different, are each chosen from a hydrogen atom, methyl, hydroxyl, acetoxy and amino residues, monoalkylamine residues and dialkylamine residues which are optionally interrupted by at least one nitrogen atom and/or optionally substituted with at least one group chosen from amine, hydroxyl, carboxyl, alkylthio and sulphonic groups, alkylthio residues wherein the alkyl group bears at least one amino residue, at least one of the radicals $R_{26}$, $R_{27}$ and $R_{28}$ being, in this case, a hydrogen atom;

or, if q=1, $R_{26}$, $R_{27}$ and $R_{28}$ are each a hydrogen atom, as well as the salts formed by these compounds with bases or acids.

These polymers can be chosen, for example, from polymers comprising from 0% to 20% by weight of units (XXIX), from 40% to 50% by weight of units (XXX) and from 40% to 50% by weight of units (XXXI) wherein $R_{25}$ is the radical —$CH_2$—$CH_2$—.

(6) Polymers derived from the N-carboxyalkylation of chitosan, such as N-carboxymethylchitosan or N-carboxybutylchitosan sold under the name "EVALSAN" by the company Jan Dekker.

(7) Polymers corresponding to the general formula (XXXII) as described, for example, in French Patent No. 1 400 366:

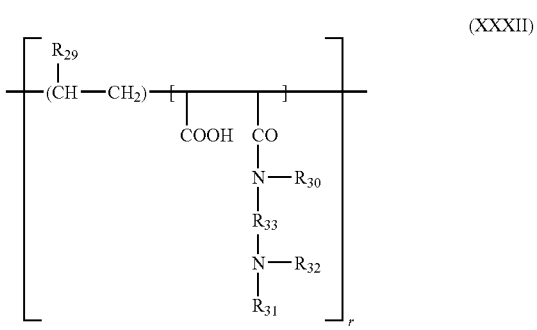

(XXXII)

wherein $R_{29}$ is chosen from a hydrogen atom, $CH_3O$, $CH_3CH_2O$ and phenyl radicals, $R_{30}$ is chosen from a hydrogen atom and lower alkyl radicals such as methyl and ethyl, $R_{31}$ is chosen from a hydrogen atom and lower alkyl radicals such as methyl and ethyl, $R_{32}$ is chosen from lower alkyl radicals such as methyl or ethyl or radicals corresponding to the formula: —$R_{33}$—$N(R_{31})_2$, $R_{33}$ is chosen from —$CH_2$—$CH_2$—, —$CH_2$—$CH_2$—$CH_2$— and —$CH_2CH(CH_3)$— groups, and $R_{31}$ having the meanings mentioned above, as well as the higher homologues of these radicals and comprising up to 6 carbon atoms, r is such that the molecular weight ranges, for example, from 500 to 6 000 000 and further, for example, ranges from 1000 to 1 000 000.

(8) Amphoteric polymers of the formula -D-X-D-X— chosen from:

a) polymers obtained by the action of chloroacetic acid or sodium chloroacetate on compounds comprising at least one unit of formula:

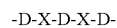

-D-X-D-X-D-    (XXXIII)

wherein D is a radical

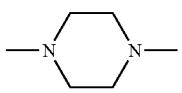

and X is chosen from the symbols E and E', E or E', which may be identical or different, are each chosen from divalent alkylene radicals comprising at least one chain chosen from straight and branched chains comprising up to 7 carbon atoms in the main chain, wherein the divalent alkylene radicals are optionally substituted with at least one hydroxyl group and which can additionally comprise at least one entity chosen from oxygen, nitrogen and sulphur atoms, and 1 to 3 aromatic and heterocyclic rings; the oxygen, nitrogen and sulphur atoms being present in the form of at least one group chosen from ether, thioether, sulphoxide, sulphone, sulphonium, alkylamine and alkenylamine groups, hydroxyl, benzylamine, amine oxide, quaternary ammonium, amide, imide, alcohol, ester and urethane groups;

b) polymers of formula:

-D-X-D-X— (XXXIV)

wherein D is a radical

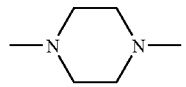

and X is chosen from the symbols E and E' and wherein at least one X is chosen from E'; E having the meaning given above and E' is chosen from divalent alkylene radicals comprising at least one chain chosen from straight and branched chains comprising up to 7 carbon atoms in the main chain, wherein the divalent alkylene radicals are optionally substituted with at least one hydroxyl radical. E' can also comprise at least one nitrogen atom, the nitrogen atom being substituted with an alkyl chain which is optionally interrupted by an oxygen atom, wherein the alkyl chain comprises at least one functional group chosen from carboxyl functional groups and hydroxyl functional groups and wherein the alkyl chain is betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

In one embodiment, the amphoteric polymers that can be used in the composition disclosed herein can be chosen from those polymers of family (1).

As used herein, the amphoteric substantive polymers may, for example, be present in an amount ranging from 0.01% to 10% by weight, relative to the total weight of the composition, further, for example, from 0.05% to 5% by weight, relative to the total weight of the composition, and even further, for example, from 0.1% to 3% by weight, relative to the total weight of the composition.

Surfactants

The compositions disclosed herein may, for example, comprise at least one surfactant.

The at least one surfactant may, for example, be chosen from anionic, amphoteric, non-ionic, zwitterionic and cationic surfactants. However, the anionic surfactants will differ from the at least one $C_{14}$-$C_{30}$ alkyl sulphate disclosed herein.

The at least one surfactant may, for example, be chosen from non-ionic surfactants.

The at least one surfactant that can, for example, be used in the composition disclosed herein may be chosen from the following:

(i) Anionic Surfactant(s):

The anionic surfactants which can be used, alone or as mixtures, in the composition disclosed herein, may be chosen from salts (such as alkali metal salts, for example, sodium salts, ammonium salts, amine salts, amino alcohol salts and magnesium salts) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffin-sulphonates; ($C_6$-$C_{24}$)alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates; ($C_6$-$C_{24}$)acyl sarcosinates and ($C_6$-$C_{24}$)acyl glutamates. It is also possible to use the carboxylic esters of ($C_6$-$C_{24}$)alkyl polyglycosides, such as alkylglucoside citrates, alkylpolyglycoside tartrates and alkylpolyglycoside sulphosuccinates, alkylsulphosuccinamates; acyl isethionates and N-acyltaurates, the alkyl or acyl radical of all of these various compounds, for example, comprising from 12 to 20 carbon atoms, and the aryl radical is chosen, for example, phenyl and benzyl groups. The anionic surfactants may also, for example, be chosen from fatty acid salts such as the salts of oleic, ricinoleic, palmitic and stearic acids, coconut oil acid and hydrogenated coconut oil acid; acyl lactylates in which the acyl radical comprises from 8 to 20 carbon atoms. At least one of alkyl-D-galactosideuronic acids and salts thereof, polyoxyalkylenated ($C_6$-$C_{24}$)alkyl ether carboxylic acids, polyoxyalkylenated ($C_6$-$C_{24}$)alkyl aryl ether carboxylic acids, polyoxyalkylenated ($C_6$-$C_{24}$)alkylamido ether carboxylic acids and salts thereof, for example, those comprising from 2 to 50 alkylene oxide, for example, ethylene oxide groups can also be used.

(ii) Non-Ionic Surfactant(s):

The non-ionic surfactants are also compounds that are well known per se (see, for example, in this respect "Handbook of Surfactants" by M. R. Porter, published by Blackie & Son (Glasgow and London), 1991, pp. 116-178) and, as used herein, their nature is not a critical feature. Thus, these surfactants can be chosen, for example, from (non-limiting list) polyethoxylated and polypropoxylated alkylphenols, alpha-diols and alcohols comprising at least one fatty chain comprising, for example, 8 to 18 carbon atoms, it being possible for the number of ethylene oxide or propylene oxide groups to range, for example, from 2 to 50. The non-ionic surfactants may also for example, be chosen from copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising on average from 1 to 5, and, for example, from 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkyl, polyglycosides, N-alkylglucamine derivatives, and amine oxides such as ($C_{10}$-$C_{14}$)alkylamine oxides and N-acylaminopropylmorpholine oxides. It will be noted that alkyl polyglycosides constitute non-ionic surfactants that can be used in the composition disclosed herein.

(iii) Amphoteric or Zwitterionic Surfactant(s):

The amphoteric or zwitterionic surfactants, whose nature is not a critical feature in the composition disclosed herein, can, for example, be chosen from <non-limiting list), aliphatic secondary and tertiary amine derivatives in which the aliphatic radical is chosen from linear and branched chains comprising from 8 to 18 carbon atoms and comprising at least one water-solubilizing anionic group (for example carboxylate, sulphonate, sulphate, phosphate or phosphonate); the amphoteric or zwitterionic surfactants may, also, for example, be chosen from $(C_8-C_{20})$alkylbetaines, sulphobetaines, $(C_8-C_{20})$alkylamido$(C_1-C_6)$alkylbetaines and $(C_8-C_{20})$alkylamido$(C_1-C_6)$alkylsulphobetaines.

The amine derivatives may, for example, be chosen from the products sold under the name MIRANOL, as described in U.S. Pat. Nos. 2,528,378 and 2,781,354 and classified in the CTFA dictionary, 3rd edition, 1982, under the names Amphocarboxyglycinates and Amphocarboxypropionates of respective structures:

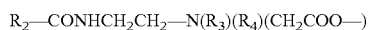

wherein: $R_2$ is chosen from linear and branched $(C_5-C_{20})$ alkyl radicals of, for example, an acid $R_2$—COOH present in hydrolyzed coconut oil; and heptyl, nonyl and undecyl radicals, $R_3$ is a beta-hydroxyethyl group and $R_4$ is a carboxymethyl group;

and

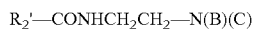

wherein:

B is chosen from groups of formula —CH$_2$CH$_2$OX', wherein C is chosen from groups of formula —(CH$_2$)$_z$—Y', with z=1 or 2, X' is chosen from a —CH$_2$CH$_2$—COOH group and a hydrogen atom, Y' is chosen from a —COOH and the —CH$_2$—CHOH—SO$_3$H radical, $R_2$' is chosen from linear and branched, saturated and unsaturated, $(C_5-C_{20})$ alkyl radicals of an acid $R_9$—COOH present, for example, in coconut oil and in hydrolysed linseed oil, alkyl radicals, for example, $C_7$, $C_9$, $C_1$ and $C_{13}$ alkyl radicals, $C_{17}$ alkyl radicals and the iso form thereof, and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name MIRANOL® C2M concentrate by the company Rhodia Chimie.

(iv) Cationic Surfactants:

The cationic surfactants may, for example, be chosen from (non-limiting list) of: primary, secondary and tertiary fatty amine salts, optionally polyoxyalkylenated; quaternary ammonium salts such as tetraalkylammonium, alkylamidoalkyl-trialkylammonium, trialkylbenzylammonium, trialkylhydroxyalkylammonium and alkylpyridinium chlorides and bromides; imidazoline derivatives; and amine oxides of cationic nature.

The at least one surfactant may, for example, be present in the composition disclosed herein in an amount ranging from 0.01% to 40% by weight, relative to the total weight of the composition, and further, for example, from 0.5% to 30% by weight, relative to the total weight of the composition.

The compositions disclosed herein may further comprise at least one supplementary thickener, i.e., non-associative rheology modifiers chosen from cellulosic thickeners (hydroxyethylcellulose, hydroxypropylcellulose, carboxymethylcellulose, etc.), guar gum and derivatives thereof (hydroxypropylguar, etc.), gums of microbial origin (xanthan gum, scleroglucan gum, etc.), and synthetic thickeners such as crosslinked homopolymers of acrylic acid and crosslinked homopolymers of acrylamido-propanesulphonic acid.

The at least one supplementary thickener may be present in an amount ranging from 0.01% to 10% by weight, relative to the total weight of the composition.

The medium of the composition, which is suitable for dyeing, may be an aqueous medium comprising water and may, for example, comprise at least one cosmetically acceptable organic solvent. For example, the at least one cosmetically acceptable organic solvent may be chosen from alcohols such as ethyl alcohol, isopropyl alcohol, benzyl alcohol and phenylethyl alcohol, and polyols and polyol ethers, such as ethylene glycol monomethyl, monoethyl and monobutyl ether, propylene glycol or ethers thereof such as, propylene glycol monomethyl ether, butylene glycol, dipropylene glycol, and also diethylene glycol alkyl, ethers such as, diethylene glycol monoethyl ether and monobutyl ether.

The at least one cosmetically acceptable solvent may, for example, be present in an amount ranging from 0.5% to 20% by weight, relative to the total weight of the composition and further, for example, from 2% to 10% by weight, relative to the total weight of the composition.

Other Ingredients

The at least one composition (A) may also comprise an effective amount of other agents, known previously elsewhere in oxidation dyeing, such as various common adjuvants, such as sequestrants such as EDTA and etidronic acid, UV screening agents, waxes, volatile and non-volatile, cyclic and linear and branched silicones, which are optionally organically modified (for example, with amine groups), preservatives, ceramides, pseudoceramides, vegetable, mineral and synthetic oils, and vitamins and provitamins, for example, panthenol.

The dyeing composition may also comprise at least one reducing agent and/or at least one antioxidant. These agents may be chosen, for example, from sodium sulphite, thioglycolic acid, thiolactic acid, sodium bisulphite, dehydroascorbic acid, hydroquinone, 2-methylhydroquinone, tert-butylhydroquinone and homogentisic acid, and, in this case, the at least one reducing agent and/or the at least one antioxidant may be present in amounts ranging from 0.05% to 1.5% by weight, relative to the total weight of the composition.

Needless to say, a person skilled in the art will take care to select the optional additional compound(s) mentioned above such that the advantageous properties intrinsically associated with the dye composition disclosed herein may not, or are not substantially, adversely affected by the envisaged addition(s).

In the ready-to-use composition or in the oxidizing composition (B), the at least one oxidizing agent may, for example, be chosen from urea peroxide, alkali metal bromates and ferricyanides, and persalts such as perborates and persulphates. In one embodiment, hydrogen peroxide can be used in the composition disclosed herein. The at least one oxidizing agent may, for example, comprise an aqueous hydrogen peroxide solution whose titre may range, for example, from 1 to 40 volumes and even further, for example, from 5 to 40 volumes.

The at least one oxidizing agent that may also be chosen from redox enzymes such as laccases, peroxidases and 2-electron oxidoreductases (such as uricase), where appropriate in the presence of their respective donor or co-factor.

The pH of the ready-to-use composition applied to the keratin fibers [composition resulting from mixing together the at least one composition (A) and the at least one composition (B)] may range, for example, from 4 to 11. It may, for example, range from 6 to 10 and may be adjusted to the desired value using at least one agent chosen from acidifying and basifying agents that are well known in the prior art in the dyeing of keratin fibers.

The basifying agents may be chosen, for example, from aqueous ammonia, alkali metal carbonates, alkanolamines such as monoethanolamine, diethanolamine and triethanolamine and derivatives thereof, oxyethylenated and oxypropylenated hydroxyalkylamines and ethylenediamines, sodium hydroxide, potassium hydroxide and the compounds of the following formula (XXXV):

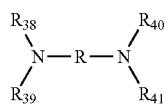

(XXXV)

wherein R is chosen from propylene residues optionally substituted by at least one entity chosen from hydroxyl groups and $C_1$-$C_4$ alkyl radical; $R_{38}$, $R_{39}$, $R_{40}$ and $R_{41}$, which may be identical or different, are each chosen from a hydrogen atom, $C_1$-$C_4$ alkyl radicals and $C_1$-$C_4$ hydroxyalkyl radicals.

The acidifying agents may, for example, be chosen from mineral and organic acids, such as hydrochloric acid, orthophosphoric acid, carboxylic acids, such as tartaric acid, citric acid and lactic acid, and sulphonic acids.

The dyeing process disclosed herein comprises applying the ready-to-use composition, prepared extemporaneously at the time of use from the compositions (A) and (B) described above, to wet or damp keratin fibers, and in leaving the composition to act for a waiting time ranging, for example, from 1 to 60 minutes, and further, for example, from 10 to 45 minutes, in rinsing the fibers and then in optionally washing them with shampoo, then rinsing them again and drying them.

One variant of this process comprises applying the dyeing composition and a composition comprising at least one oxidizing agent sequentially with a time delay or simultaneously to wet or damp keratin fibers, with an optional intermediate rinse, and in leaving the said compositions to act for an exposure time ranging from 1 to 60 minutes and then in rinsing the fibers, and then optionally in washing them with shampoo, then rinsing them again and drying them.

The example which follows is intended to illustrate the embodiments disclosed herein, but without being limiting.

EXAMPLE

The following composition was prepared (amounts given in percentages by weight):

| | |
|---|---|
| Oxyethylenated (2EO) stearyl alcohol | 4 |
| Oxyethylenated (21EO) stearyl alcohol | 3 |
| Cetylstearyl alcohol | 1 |
| Myristyl/cetyl/stearyl myristate/palmitate/stearate mixture (sold under the name SPERMWAX VEGETAL by Robeco) | 1 |
| C18-C22 alkyl sulphate (product sold under the name LANETTE by Cognis) | 1.5 |
| Fatty-chain cationic polyurethane obtained by condensing 1,3-bis(isocyanatomethylcyclohexane), N,N-dimethylethanolamine quaternized with bromododecane, N,N-dimethylethanolamine and polyoxyethylene of molecular weight 10 000 | |
| Glycerol C12 alkyl ether (1.5 mol) | 2 |
| MERQUAT 100 in 40% strength aqueous solution | 4 |
| Titanium oxide | 0.15 |
| Sodium metabisulphite | 0.71 |
| EDTA (ethylenediaminetetraacetic acid) | 0.2 |
| Tert-butylhydroquinone | 0.3 |
| 1,4-diaminobenzene | 0.2 |
| Para-aminophenol | 1.2 |
| 1,3-dihydroxybenzene | 0.1 |
| 1-hydroxy-3-aminobenzene | 0.2 |
| 1-methyl-2-hydroxy-4-β-hydroxyethylaminobenzene | 0.8 |
| Monoethanolamine | 1 |
| Aqueous ammonia containing 20% $NH_3$ | 11 |
| Perfume q.s. | |
| Demineralized water q.s. | 100 |

This composition was mixed at the time of use with an oxidizing composition in the form of an emulsion containing as an oxidizing agent 7.5% of hydrogen peroxide, in a proportion of 1 part by weight of dye composition per 1.5 parts by weight of oxidizing composition. The resulting mixture was applied to locks of natural hair containing 90% white hairs and was left to act for 30 minutes. After rinsing, washing with shampoo and drying, hair was obtained which was dyed in a sustained coppery red light chestnut shade.

What is claimed is:

1. A composition for the oxidation dyeing of keratin fibers, comprising, in a medium suitable for dyeing,
   a) at least one oxidation dye;
   b) at least one fatty alcohol;
   c) at least one associative polymer chosen from non-ionic, anionic, cationic, and amphoteric associative polymers;
   wherein the non-ionic associative polymers are chosen from:
   (1) celluloses modified with groups comprising at least one fatty chain;
   (2) hydroxypropylguars modified with groups comprising at least one fatty chain;
   (3) polyurethane polyethers comprising in their chain both polyoxyethylenated hydrophilic blocks and hydrophobic blocks which are aliphatic sequences alone and/or cycloaliphatic and/or aromatic sequences;
   (4) copolymers of vinylpyrrolidone and of fatty-chain hydrophobic monomers;
   (5) copolymers of $C_1$-$C_6$ alkyl methacrylates or acrylates and of amphiphilic monomers comprising at least one fatty chain; and
   (6) copolymers of hydrophilic methacrylates or acrylates and of hydrophobic monomers comprising at least one fatty chain; and
   d) at least one $C_{14}$-$C_{30}$ alkyl sulphate; and
   wherein the ratio, by weight, of the at least one $C_{14}$-$C_{30}$ alkyl sulphate to the at least one associative polymer ranges from 0.1:1 to 10:1.

2. The composition according to claim 1, wherein the keratin fibers are human keratin fibers.

3. The composition according to claim 2, wherein the human keratin fibers are hair.

4. The composition according to claim 1, wherein the at least one $C_{14}$-$C_{30}$ alkyl sulphate is chosen from sodium cetostearyl sulphate and sodium myristyl sulphate.

5. The composition according to claim 1, wherein the at least one $C_{14}$-$C_{30}$ alkyl sulphate is present in an amount ranging from 0.1% to 10% by weight, relative to the total weight of the composition.

6. The composition according to claim 5, wherein the at least one $C_{14}$-$C_{30}$ alkyl sulphate is present in an amount ranging from 0.5% to 5% by weight, relative to the total weight of the composition.

7. The composition according to claim 1, wherein the at least one associative polymer is chosen from anionic polymers comprising at least one fatty chain.

8. The composition according to claim 7, wherein the anionic polymers comprising at least one fatty chain are chosen from polymers comprising at least one hydrophilic unit and at least one fatty-chain allyl ether unit.

9. The composition according to claim 8, wherein the at least one hydrophilic unit comprises at least one ethylenic unsaturated anionic monomer.

10. The composition according to claim 9, wherein the at least one hydrophilic unit is a vinylcarboxylic acid.

11. The composition according to claim 8, wherein the at least one fatty-chain allyl ether unit is chosen from monomers of formula (I) below:

$$CH_2=CR'CH_2OB_nR \quad (I)$$

wherein:

R' is chosen from H and $CH_3$;

B is an ethyleneoxy radical;

n is equal to zero or is an integer ranging from 1 to 100; and

R is a hydrocarbon-based radical chosen from alkyl, arylalkyl, aryl, alkylaryl and cycloalkyl radicals, comprising from 8 to 30 carbon atoms.

12. The composition according to claim 11, wherein, in formula (I), R is a hydrocarbon-based radical comprising from 10 to 24 carbon atoms.

13. The composition according to claim 12, wherein, in formula (I), R is a hydrocarbon-based radical comprising from 12 to 18 carbon atoms.

14. The composition according to claim 7, wherein the anionic polymers comprising at least one fatty chain are chosen from polymers comprising at least one hydrophilic unit of unsaturated olefinic carboxylic acid and at least one hydrophobic unit of unsaturated carboxylic acid $(C_{10}$-$C_{30})$alkyl ester.

15. The composition according to claim 14, wherein the at least one hydrophilic unit of unsaturated olefinic carboxylic acid is chosen from monomers of formula (II) below:

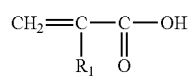

(II)

wherein $R_1$ is chosen from H, $CH_3$, and $C_2H_5$, and wherein the at least one hydrophobic unit of unsaturated carboxylic acid $(C_{10}$-$C_{30})$alkyl ester is chosen from monomers of formula (III) below:

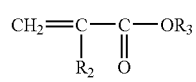

(III)

wherein:

$R_2$ is chosen from H, $CH_3$, and $C_2H_5$; and $R_3$ is chosen from $C_{10}$-$C_{30}$ alkyl radicals.

16. The composition according to claim 15 wherein, in formula (III), $R_3$ is chosen from $C_{12}$-$C_{22}$ alkyl radicals.

17. The composition according to claim 7, wherein the anionic polymers comprising at least one fatty chain are chosen from maleic anhydride/$C_{30}$-$C_{38}$ α-olefin/alkyl maleate terpolymers.

18. The composition according to claim 7, wherein the anionic polymers comprising at least one fatty chain are chosen from acrylic terpolymers comprising:

(a) from 20% to 70% by weight of a carboxylic acid containing α,β-monoethylenic unsaturation;

(b) from 20% to 80% by weight of a non-surfactant monomer containing α,β-monoethylenic unsaturation and being other than (a); and (c) from 0.5% to 60% by weight of a non-ionic monourethane which is the product of reaction of a monohydric surfactant with a monoisocyanate containing monoethylenic unsaturation.

19. The composition according to claim 7, wherein the anionic polymers comprising at least one chain are chosen from copolymers comprising among their monomers at least one carboxylic acid containing α,β-monoethylenic unsaturation and at least one ester of carboxylic acid containing α,β-monoethylenic unsaturation and of an oxyalkylenated fatty alcohol.

20. The composition according to claim 1, wherein the polyurethane polyethers comprise at least two hydrocarbon-based lipophilic chains comprising from 8 to 30 carbon atoms, separated by a hydrophilic block, and wherein the hydrocarbon-based chains are pendent chains or chains at the end of the hydrophilic block.

21. The composition according to claim 1, wherein the polyurethane polyethers are in multiblock form.

22. The composition according to claim 21, wherein The polyurethane polyethers are in triblock form.

23. The composition according to claim 1, wherein the at least one associative polymer is chosen from cationic polymers comprising at least one fatty chain.

24. The composition according to claim 23, wherein the cationic polymers comprising at least one fatty chain are chosen from cationic polyurethanes.

25. The composition according to claim 1, wherein the at least one associative polymer is chosen from cationic polymers comprising at least one fatty chain and is chosen from:

(i) quaternized celluloses modified with at least one group comprising at least one fatty chain;

(ii) quaternized hydroxyethylcelluloses modified with at least one group comprising at least one fatty chain;

(iii) cationic polyurethanes;

(iv) cationic polyvinyllactams; and (v) acrylic terpolymers comprising acrylates, amino(meth)acrylates and $C_{10}$-$C_{30}$ alkyl itaconates, polyoxyethylenated with 20 mol of ethylene oxide.

26. The composition according to claim 25, wherein the at least one group of the quaternized celluloses and hydroxyethylcelluloses, which may be identical or different, are each chosen from alkyl groups comprising from 8 to 30 carbon atoms.

27. The composition according to claim 26, wherein the cationic polymers comprising at least one fatty chain are chosen from quaternized hydroxyethylcellulose modified with at least one group chosen from $C_{12}$ and $C_{18}$ alkyl groups.

28. The composition according to claim 25, wherein the cationic polymers comprising at least one fatty chain are chosen from polymers of formula (IV) below:

$$R—X—(P)_n\text{-}[L\text{-}(Y)_m]_r\text{-}L'\text{-}(P')_p—X'\text{-}R' \qquad (IV)$$

wherein:
- R and R', which may be identical or different, are each chosen from hydrophobic groups and a hydrogen atom;
- X and X', which may be identical or different, are each chosen from groups comprising at least one amine functional group optionally bearing at least one hydrophobic group, or alternatively groups L";
- L, L' and L", which may be identical or different, are each chosen from groups derived from a diisocyanate;
- P and P', which may be identical or different, are each chosen from groups comprising at least one amine functional group optionally bearing at least one hydrophobic group;
- Y is chosen from hydrophilic groups;
- r is an integer ranging from 1 to 100, and
- n, m and p, which may be identical or different, are each integers ranging from 0 to 1000; and wherein
- the molecule comprises at least one functional group chosen from protonated and quaternized amine functional groups and hydrophobic groups.

29. The composition according to claim 28, wherein, in formula (IV), r is an integer ranging from 1 to 50.

30. The composition according to claim 28, wherein, in formula (IV), r is an integer ranging from 1 to 25.

31. The composition according to claim 1, wherein the at least one associative polymer is chosen from amphoteric polymers comprising at least one fatty chain comprising from 8 to 30 carbon atoms and at least one non-cyclic cationic unit.

32. The composition according to claim 31, wherein the amphoteric polymers comprise from 1 to 20 mol % of monomer comprising at least one fatty chain, relative to the total number of moles of monomers.

33. The composition according to claim 32, wherein the amphoteric polymers comprise:
1) at least one monomer of formula (IXa) or (IXb):

$$R_1—CH\!=\!\underset{R_2}{\overset{}{C}}—\underset{\parallel}{\overset{}{C}}—Z—(C_nH_{2n})—\overset{R_3}{\underset{R_4}{N^+}}—R_5 \quad A^- \qquad (IXa)$$

$$R_1—CH\!=\!\underset{R_2}{\overset{}{C}}—\underset{\parallel}{\overset{}{C}}—Z—(C_nH_{2n})—N\!\!\begin{array}{c}R_3\\R_4\end{array} \qquad (IXb)$$

wherein:
- $R_1$ and $R_2$, which may be identical or different, are each chosen from a hydrogen atom and a methyl radical;
- $R_3$, $R_4$ and $R_5$, which may be identical or different, are each chosen from linear and branched alkyl radicals comprising from 1 to 30 carbon atoms;
- Z is chosen from a NH group and an oxygen atom;
- n is an integer ranging from 2 to 5; and
- $A^-$ is chosen from anions derived from organic or mineral acids;

2) at least one monomer of formula (X)

$$R_6—CH\!=\!CR_7—COOH \qquad (X)$$

wherein $R_6$ and $R_7$, which may be identical or different, are each chosen from a hydrogen atom and a methyl radical; and 3) at least one monomer of formula (XI):

$$R_6—CH\!=\!CR_7—COXR_8 \qquad (XI)$$

wherein:
- $R_6$ and $R_7$, which may be identical or different, are each chosen from a hydrogen atom and a methyl radical;
- X is chosen from an oxygen atom and a nitrogen atom; and
- $R_8$ is chosen from linear and branched alkyl radicals comprising from 1 to 30 carbon atoms; wherein at least one of the monomers of formula (IXa), (IXb) or (XI) comprise at least one fatty chain.

34. The composition according to claim 33, wherein the monomers of formulae (IXa) and (IXb) are chosen from dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, wherein these monomers are optionally quaternized.

35. The composition according to claim 33, wherein the monomers of formula (IXa) are chosen from acrylamidopropyltrimethylammonium chloride and methacrylamidopropyltrimethylammonium chloride.

36. The composition according to claim 33, wherein the monomers of formula (X) are chosen from acrylic acid, methacrylic acid, crotonic acid and 2-methylcrotonic acid.

37. The composition according to claim 33, wherein the monomers of formula (XI) are chosen from $C_{12}$-$C_{22}$ acrylates and methacrylates.

38. The composition according to claim 37, wherein the monomers of formula (XI) are chosen from $C_{16}$-$C_{18}$ alkyl acrylates and methacrylates.

39. The composition according to claim 1, wherein the at least one associative polymer is present in an amount ranging from 0.05% to 10% by weight, relative to the total weight of the composition.

40. The composition according to claim 39, wherein the at least one associative polymer is present in an amount ranging from 0.1% to 5% by weight, relative to the total weight of the composition.

41. The composition according to claim 1, wherein the ratio, by weight, of the at least one $C_{14}$-$C_{30}$ alkyl sulphate to the at least one associative polymer ranges from 0.5:1 to 5:1.

42. The composition according to claim 1, wherein the at least one oxidation dye is chosen from oxidation bases and couplers.

43. The composition according to claim 42, wherein the at least one oxidation dye is chosen from oxidation bases.

44. The composition according to claim 43, wherein the oxidation bases are chosen from ortho- and para-phenylenediamines, double bases, ortho- and para-aminophenols, heterocyclic bases, and the acid addition salts thereof.

45. The composition according to claim 44, wherein the para-phenylenediamines are chosen from compounds of formula (XII) below and the acid addition salts thereof:

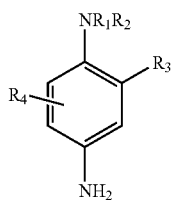

(XII)

wherein:
- R$_1$ is chosen from a hydrogen atom, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals and C$_1$-C$_4$ alkyl radicals substituted with at least one group chosen from nitrogenous, phenyl and 4'-aminophenyl groups;
- R$_2$ is chosen from a hydrogen atom, C$_1$-C$_4$ alkyl radicals, C$_1$-C$_4$ monohydroxyalkyl radicals, C$_2$-C$_4$ polyhydroxyalkyl radicals, (C$_1$-C$_4$)alkoxy(C$_1$-C$_4$)alkyl radicals and C$_1$-C$_4$ alkyl radicals substituted with at least one nitrogenous group; R$_1$ and R$_2$ may also form, together with the nitrogen atom that bears them, at least one heterocycle chosen from 5- and 6-membered nitrogen heterocycles optionally substituted with at least one group chosen from alkyl, hydroxyl and ureido groups;
- R$_3$ is chosen from a hydrogen atom, halogen atoms, C$_1$-C$_4$ alkyl radicals, sulpho radicals, carboxyl radicals, C$_1$-C$_4$ monohydroxyalkyl radicals, C$_1$-C$_4$ hydroxyalkoxy radicals, acetylamino(C$_1$-C$_4$)alkoxy radicals, mesylamino(C$_1$-C$_4$)alkoxy radicals and carbamoylamino(C$_1$-C$_4$)alkoxy radicals; and
- R$_4$ is chosen from a hydrogen atom, halogen atoms and C$_1$-C$_4$ alkyl radicals.

46. The composition according to claim 44, wherein the double bases are chosen from compounds of formula (XIII) below and the acid addition salts thereof:

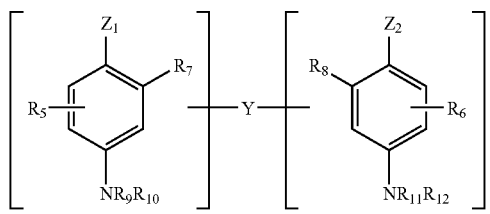

(XIII)

wherein:
- Z$_1$ and Z$_2$, which may be identical or different, are each chosen from hydroxyl and —NH$_2$ radicals which may be substituted with at least one entity chosen from C$_1$-C$_4$ alkyl radicals and linking arm Y;
- linking arm Y is chosen from linear and branched alkylene chains comprising from 1 to 14 carbon atoms, which may be interrupted by or terminated with at least one entity chosen from nitrogenous groups and heteroatoms, and optionally substituted with at least one radical chosen from hydroxyl radicals and C$_1$-C$_6$ alkoxy radicals;
- R$_5$ and R$_6$, which may be identical or different, are each chosen from a hydrogen atom, halogens, C$_1$-C$_4$ alkyl radicals, C$_1$-C$_4$ monohydroxyalkyl radicals, C$_2$-C$_4$ polyhydroxyalkyl radicals, C$_1$-C$_4$ aminoalkyl radicals, and linking arm Y; and
- R$_7$, R$_8$, R$_9$, R$_{10}$, R$_{11}$ and R$_{12}$, which may be identical or different, are each chosen from a hydrogen atom, linking arm Y, and C$_1$-C$_4$ alkyl radicals;

provided that the compounds of formula (XIII) comprise only one linking arm Y per molecule.

47. The composition according to claim 44, wherein the para-aminophenols are chosen from compounds of formula (XIV) below and the acid addition salts thereof:

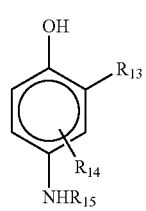

(XIV)

wherein:
- R$_{13}$ is chosen from a hydrogen atom, halogen atoms, C$_1$-C$_4$ alkyl, C$_1$-C$_4$ monohydroxyalkyl, (C$_1$-C$_4$)alkoxy(C$_1$-C$_4$) alkyl, C$_1$-C$_4$ aminoalkyl and hydroxy-(C$_1$-C$_4$)alkylamino(C$_1$-C$_4$)alkyl radicals,
- R$_{14}$ is chosen from a hydrogen atom, halogen atoms, C$_1$-C$_4$ alkyl, C$_1$-C$_4$ monohydroxyalkyl, C$_2$-C$_4$ polyhydroxyalkyl, C$_1$-C$_4$ aminoalkyl, C$_1$-C$_4$ cyanoalkyl and (C$_1$-C$_4$) alkoxy(C$_1$-C$_4$)alkyl radicals, and
- R$_{15}$ is chosen from a hydrogen atom and C$_1$-C$_4$ alkyl radicals.

48. The composition according to claim 47, wherein, in formula (XIV), R$_{13}$ is a fluorine atom.

49. The composition according to claim 48, wherein, in formula (XIV), R$_{14}$ is a halogen atom.

50. The composition according to claim 44, wherein the heterocyclic bases are chosen from pyridine derivatives, pyrimidine derivatives, and pyrazole derivatives.

51. The composition according to claim 41, wherein the oxidation bases are present in an amount ranging from 0.0005% to 12% by weight, relative to the total weight of the composition.

52. The composition according to claim 51, wherein the oxidation bases are present in an amount ranging from 0.005% to 8% by weight, relative to the total weight of the composition.

53. The composition according to claim 42, wherein the couplers are chosen from meta-phenylenediamines, meta-aminophenols, meta-diphenols, heterocyclic couplers, and the acid addition salts thereof.

54. The composition according to claim 42, wherein the couplers are present in an amount ranging from 0.0001% to 10% by weight, relative to the total weight of the composition.

55. The composition according to claim 54, wherein the couplers are present in an amount ranging from 0.005% to 5% by weight, relative to the total weight of the composition.

56. The composition according to claim 44, wherein the acid addition salts of the oxidation bases are chosen from hydrochlorides, hydrobromides, sulphates, tartrates, lactates and acetates.

57. The composition according to claim 53, wherein the acid addition salts of the couplers are chosen from hydrochlorides, hydrobromides, sulphates, tartrates, lactates and acetates.

58. The composition according to claim 1, further comprising at least one direct dye.

59. The composition according to claim 1, wherein the at least one fatty alcohol is chosen from oxyalkylenated and glycerolated fatty alcohols.

60. The composition according to claim 59, wherein the oxyalkylenated fatty alcohols are chosen from linear and branched, saturated and unsaturated fatty alcohols, and comprise from 10 to 20 carbon atoms and from 2 to 40 ethylene oxide groups.

61. The composition according to claim 59, wherein the glycerolated fatty alcohols are chosen from linear and branched, saturated and unsaturated fatty alcohols, and comprise from 8 to 40 carbon atoms and from 1 to 30 glycerol groups.

62. The composition according to claim 1, wherein the at least one fatty alcohol is present in an amount ranging from 0.05% to 30% by weight, relative to the total weight of the composition.

63. The composition according to claim 61, wherein the at least one fatty alcohol is present in an amount ranging from 0.5% to 20% by weight, relative to the total weight of the composition.

64. The composition according to claim 1, further comprising at least one additional polymer chosen from amphoteric and cationic substantive polymers different that the at least one associative polymer.

65. The composition according to claim 64, wherein the at least one additional polymer is the homopolymer of dimethyldiallylammonium chloride.

66. The composition according to claim 65, wherein at least one additional polymer is chosen from polymers comprising repeating units corresponding to formula (XXIV) below:

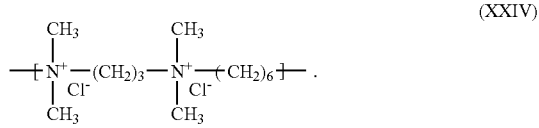

67. The composition according to claim 64, wherein the at least one additional polymer is chosen from polymers comprising repeating units corresponding to formula (XXV) below:

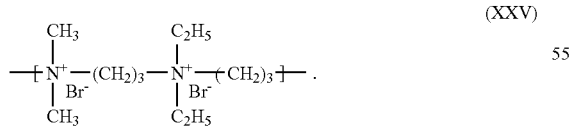

68. The composition according to claim 64, wherein the at least one additional polymer is present in an amount ranging from 0.01% to 10% by weight, relative to the total weight of the composition.

69. The composition according to claim 68, wherein the at least one additional polymer is present in an amount ranging from 0.05% to 5% by weight, relative to the total weight of the composition.

70. The composition according to claim 69, wherein the at least one additional polymer is present in an amount ranging from 0.1% to 3% by weight, relative to the total weight of the composition.

71. The composition according to claim 1, further comprising at least one surfactant chosen from anionic, amphoteric, non-ionic, zwitterionic and cationic surfactants.

72. The composition according to claim 71, wherein the at least one surfactant is chosen from non-ionic surfactants.

73. The composition according to claim 72, wherein the at least one surfactant is present in an amount ranging from 0.01% to 40% by weight, relative to the total weight of the composition.

74. The composition according to claim 73, wherein the at least one surfactant is present in an amount ranging from 0.5% to 30% by weight, relative to the total weight of the composition.

75. The composition according to claim 1, further comprising at least one supplementary thickener.

76. The composition according to claim 75, wherein the at least one supplementary thickener is chosen from cellulosic thickeners, guar gum derivatives, gums of microbial origin, and synthetic thickeners.

77. The composition according to claim 76, wherein the at least one supplementary thickener is present in an amount ranging from 0.01% to 10% by weight, relative to the total weight of the composition.

78. The composition according to claim 1, further comprising at least one reducing agent, present in an amount ranging from 0.05% to 1.5% by weight, relative to the total weight of the composition.

79. A ready-to-use composition comprising, in a medium suitable for dyeing,
 a) at least one oxidation dye,
 b) at least one fatty alcohol,
 c) at least one associative polymer chosen from non-ionic, anionic, cationic, and amphoteric associative polymers;
 wherein the non-ionic associative polymers are chosen from:
  (1) celluloses modified with groups comprising at least one fatty chain;
  (2) hydroxypropylguars modified with groups comprising at least one fatty chain;
  (3) polyurethane polyethers comprising in their chain both polyoxyethylenated hydrophilic blocks and hydrophobic blocks which are aliphatic sequences alone and/or cycloaliphatic and/or aromatic sequences;
  (4) copolymers of vinylpyrrolidone and of fatty-chain hydrophobic monomers;
  (5) copolymers of $C_1$-$C_6$ alkyl methacrylates or acrylates and of amphiphilic monomers comprising at least one fatty chain; and
  (6) copolymers of hydrophilic methacrylates or acrylates and of hydrophobic monomers comprising at least one fatty chain,
 d) at least one $C_{14}$-$C_{30}$ alkyl sulphate, and
 e) at least one oxidizing agent; and
wherein the ratio, by weight, of the at least one $C_{14}$-$C_{30}$ alkyl sulphate to the at least one associative polymer ranges from 0.1:1 to 10:1.

80. The ready-to-use composition according to claim 79, wherein the at least one oxidizing agent is chosen from hydrogen peroxide, urea peroxide, alkali metal bromates and ferricyanides, persalts, and redox enzymes together where appropriate with the respective donor or co-factor thereof.

81. The ready-to-use composition according to claim 80, wherein the at least one oxidizing agent is hydrogen peroxide.

82. The ready-to-use composition according to claim 81, wherein the at least one oxidizing agent is an aqueous hydrogen peroxide solution whose titre ranges from 1 to 40 volumes.

83. The ready-to-use composition according to claim 82, wherein the composition has a pH ranging from 4 to 11.

84. A process for the oxidation dyeing of keratin fibers comprising:
(i) applying to the keratin fibers at least one composition (A) comprising, in a medium suitable for dyeing,
  a) at least one oxidation dye;
  b) at least one fatty alcohol;
  c) at least one associative polymer chosen from non-ionic, anionic, cationic and amphoteric associative polymers;
wherein the non-ionic associative polymers are chosen from:
  (1) celluloses modified with groups comprising at least one fatty chain;
  (2) hydroxpropylguars modified with groups comprising at least one fatty chain;
  (3) polyurethane polyethers comprising in their chain both polyoxyethylenated hydrophilic blocks and hydrophobic blocks which are aliphatic sequenecs alone and/or cycloaliphatic and/or aromatic sequences;
  (4) copolymers of vinylpyrrolidone and of fatty-chain hydrophobic monomers;
  (5) copolymers of $C_1$-$C_6$ alkyl methacrylates or acrylates and of amphiphilic monomers comprising at least one fatty chain; and
  (6) copolymers of hydrophilic methacrylates or acrylates and of hydrophobic monomers comprising at least one fatty chain; and
  d) at least one $C_{14}$-$C_{30}$ alkyl sulphate, and
wherein the ratio, by weight, of the at least one $C_{14}$-$C_{30}$ alkyl sulphate to the at least one associative polymer ranges from 0.1:1 to 10:1; and
(ii) applying to the keratin fibers at least one composition (B) comprising at least one oxidizing agent.

85. The process according to claim 84, wherein the keratin fibers are hair.

86. The process according to claim 83, comprising mixing, at the time of use, the at least one composition (A) and the at least one composition (B).

87. The process according to claim 83, wherein the at least one composition (B) is applied sequentially before or after the at least one composition (A), with or without intermediate rinsing.

88. The process according to claim 83, wherein the color of the fibers is developed at an alkaline, neutral or acidic pH.

89. A multicompartment kit comprising:
(i) a first compartment comprising at least one composition (A) comprising, in a medium suitable for dyeing,
  a) at least one oxidation dye;
  b) at least one fatty alcohol;
  c) at least one associative polymer chosen from non-ionic, anionic, cationic, and amphoteric associative polymers;
wherein the non-ionic associative polymers are chosen from:
  (1) celloloses modified with groups comprising at least one fatty chain;
  (2) hydroxypropylguars modified with groups comprising at least one fatty chain;
  (3) polyurethane polyethers comprising in their chain both polyoxyethlenated hydrophilic blocks and hydrophobic blocks which are aliphatic sequences alone and/or cycloaliphatic and/or aromatic sequences;
  (4) copolymers of vinylpyrrolidone and of fatty-chain hydrophobic monomers;
  (5) copolymers of $C_1$-$C_6$ alkyl methacrylates or acrylates and of amphiphilic monomers comprising at least one fatty chain; and
  (6) copolymers of hydrophilic methacrylates or acrylates and of hydrophobic monomers comprising at least one fatty chain; and
  d) at least one $C_{14}$-$C_{30}$ alkyl sulphate; and
wherein the ratio, by weight, of the at least one $C_{14}$-$C_{+}$alkyl sulphate to the at least one associative polymer ranges from 0.1:1 to 10:1, and
(ii) a second compartment comprising at least one composition (B) comprising at least one oxidizing agent.

* * * * *

UNITED STATES PATENT AND TRADEMARK OFFICE
CERTIFICATE OF CORRECTION

PATENT NO. : 7,695,526 B2
APPLICATION NO. : 11/907406
DATED : April 13, 2010
INVENTOR(S) : Luc Nicolas-Morgantini et al.

It is certified that error appears in the above-identified patent and that said Letters Patent is hereby corrected as shown below:

Title page, item (54), line 6 of Title, "C14-C30" should read --$C_{14}$-$C_{30}$--.

Claim 89, col. 52, line 36, "$C_{14}$-$C_{+}$alkyl" should read --$C_{14}$-$C_{30}$ alkyl--.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,695,526 B2  Page 1 of 1
APPLICATION NO. : 11/907406
DATED : April 13, 2010
INVENTOR(S) : Luc Nicolas-Morgantini et al.

It is certified that error appears in the above-identified patent and that said Letters Patent is hereby corrected as shown below:

Title page, item (54), line 6 and at Column 1, line 6, of Title, "C14-C30" should read --$C_{14}$-$C_{30}$--.

Claim 89, col. 52, line 36, "$C_{14}$-$C_+$alkyl" should read --$C_{14}$-$C_{30}$ alkyl--.

This certificate supersedes the Certificate of Correction issued June 22, 2010.

Signed and Sealed this

Twentieth Day of July, 2010

David J. Kappos
*Director of the United States Patent and Trademark Office*